US011602592B2

(12) United States Patent
Johnson et al.

(10) Patent No.: US 11,602,592 B2
(45) Date of Patent: Mar. 14, 2023

(54) ENDOVASCULAR PERFUSION AUGMENTATION FOR CRITICAL CARE

(71) Applicants: THE REGENTS OF THE UNIVERSITY OF CALIFORNIA, Oakland, CA (US); Government of the United States as Represented by the Secretary of the Air Force, Wright-Patterson AFB, OH (US)

(72) Inventors: Michael Austin Johnson, Sacramento, CA (US); Lucas Paul Neff, Decatur, GA (US); Timothy Williams, Travis AFB, CA (US)

(73) Assignees: The Regents of the University of California, Oakland, CA (US); Government Of The United States As Represented By The Secretary Of The Air Force, Wright-Patterson AFB, OH (US)

( * ) Notice: Subject to any disclaimer, the term of this patent is extended or adjusted under 35 U.S.C. 154(b) by 724 days.

(21) Appl. No.: 16/507,938

(22) Filed: Jul. 10, 2019

(65) Prior Publication Data

US 2020/0038566 A1 Feb. 6, 2020

Related U.S. Application Data

(63) Continuation of application No. PCT/US2018/013413, filed on Jan. 11, 2018.
(Continued)

(51) Int. Cl.
*G08B 21/04* (2006.01)
*A61M 5/142* (2006.01)
*A61M 25/10* (2013.01)

(52) U.S. Cl.
CPC ...... *A61M 5/142* (2013.01); *A61M 25/10184* (2013.11); *A61M 25/1011* (2013.01);
(Continued)

(58) Field of Classification Search
USPC ...... 340/539.12, 539.22, 539.24, 539.3, 578, 340/600–601, 618, 661, 665, 691.6,
(Continued)

(56) References Cited

U.S. PATENT DOCUMENTS

| 2,156,289 A | 5/1939 | Hoy |
| 4,464,172 A | 8/1984 | Lichtenstein |

(Continued)

FOREIGN PATENT DOCUMENTS

| AU | 2014223477 B2 | 9/2014 |
| AU | 2014223556 B2 | 9/2014 |

(Continued)

OTHER PUBLICATIONS

Williams et al., "Extending REBOA: Endovascular Variable Aortic Control (EVAC) in a Lethal Model of Hemorrhagic Shock", Journal of Trauma and Acute Care Surgery, vol. 81, No. 2, Aug. 2016, pp. 294-301.
(Continued)

*Primary Examiner* — Daniel Previl
(74) *Attorney, Agent, or Firm* — Kilpatrick Townsend & Stockton LLP

(57) ABSTRACT

Systems and methods for Endovascular Perfusion Augmentation for Critical Care (EPACC) are provided. The system may include a catheter having an expandable aortic blood flow regulation device disposed on the distal end of the catheter for placement within an aorta of a patient. The system may also include a catheter controller unit that causes the expandable aortic blood flow regulation device to expand and contract to restrict blood flow through the aorta.
(Continued)

The system may also include one or more sensors for measuring physiological information indicative of blood flow through the aorta, and a non-transitory computer readable media having instructions stored thereon, wherein the instructions, when executed by a processor coupled to the one or more sensors, cause the processor to compare the measured physiological information with a target physiological range associated with blood flow through the aorta such that the catheter controller unit automatically adjusts expansion and contraction of the expandable aortic blood flow regulation device to adjust an amount of blood flow through the aorta if the measured physiological information falls outside the target physiological range.

20 Claims, 16 Drawing Sheets

Related U.S. Application Data

(60) Provisional application No. 62/445,551, filed on Jan. 12, 2017.

(52) U.S. Cl.
CPC .............. *A61M 25/10182* (2013.11); *A61M 2005/14208* (2013.01); *A61M 2205/05* (2013.01); *A61M 2205/3331* (2013.01); *A61M 2205/3584* (2013.01); *A61M 2210/127* (2013.01); *A61M 2230/06* (2013.01); *A61M 2230/205* (2013.01); *A61M 2230/208* (2013.01); *A61M 2230/30* (2013.01); *A61M 2230/42* (2013.01); *A61M 2230/50* (2013.01)

(58) Field of Classification Search
USPC .......................................... 340/825.19, 3.63
See application file for complete search history.

(56) References Cited

U.S. PATENT DOCUMENTS

| | | | |
|---|---|---|---|
| 4,713,888 A | 12/1987 | Broselow | |
| 4,777,951 A | 10/1988 | Cribier et al. | |
| 4,823,469 A | 4/1989 | Broselow | |
| 4,865,549 A | 9/1989 | Sonsteby | |
| 4,926,885 A | 5/1990 | Hinkle | |
| 4,983,166 A | 1/1991 | Yamawaki | |
| 5,047,045 A | 9/1991 | Arney et al. | |
| 5,135,494 A | 8/1992 | Engelson et al. | |
| 5,158,529 A | 10/1992 | Kanai | |
| 5,169,386 A | 12/1992 | Becker et al. | |
| 5,282,479 A | 2/1994 | Havran | |
| 5,320,605 A | 6/1994 | Sahota | |
| 5,383,856 A | 1/1995 | Bersin | |
| 5,447,503 A | 9/1995 | Miller | |
| 5,486,192 A | 1/1996 | Walinsky et al. | |
| 5,505,702 A | 4/1996 | Arney | |
| 5,522,400 A | 6/1996 | Williams | |
| 5,571,093 A | 11/1996 | Cruz et al. | |
| 5,718,678 A | 2/1998 | Fleming, III | |
| 5,738,652 A | 4/1998 | Boyd et al. | |
| 5,911,702 A | 6/1999 | Romley et al. | |
| 6,011,988 A | 1/2000 | Lynch et al. | |
| 6,013,019 A | 1/2000 | Fischell | |
| 6,102,930 A | 8/2000 | Simmons, Jr. | |
| 6,113,579 A | 9/2000 | Eidenschink et al. | |
| 6,146,370 A | 11/2000 | Barbut | |
| 6,161,547 A | 12/2000 | Barbut | |
| 6,165,199 A | 12/2000 | Barbut | |
| 6,190,356 B1 | 2/2001 | Bersin | |
| 6,231,572 B1 | 5/2001 | Hart et al. | |
| 6,248,121 B1 | 6/2001 | Nobles | |
| 6,280,434 B1 | 8/2001 | Kinoshita et al. | |
| 6,315,768 B1 * | 11/2001 | Wallace | A61M 25/007 604/507 |
| 6,423,031 B1 | 7/2002 | Donlon | |
| 6,453,572 B2 | 9/2002 | Cross et al. | |
| 6,575,932 B1 | 6/2003 | O'Brien et al. | |
| 6,579,221 B1 | 6/2003 | Peterson | |
| 6,602,270 B2 | 8/2003 | Leschinsky et al. | |
| 6,656,153 B1 | 12/2003 | Sakai et al. | |
| 6,666,814 B2 | 12/2003 | Downey et al. | |
| 6,669,679 B1 | 12/2003 | Savage et al. | |
| 6,679,860 B2 | 1/2004 | Stiger | |
| 6,695,811 B2 | 2/2004 | Samson et al. | |
| 6,719,270 B2 | 4/2004 | Ozawa | |
| 6,719,720 B1 | 4/2004 | Voelker et al. | |
| 6,733,513 B2 | 5/2004 | Boyle et al. | |
| 6,735,532 B2 | 5/2004 | Freed et al. | |
| 6,736,790 B2 | 5/2004 | Barbut et al. | |
| 6,746,462 B1 | 6/2004 | Selmon et al. | |
| 6,796,959 B2 | 9/2004 | Davis et al. | |
| 6,936,056 B2 | 8/2005 | Nash et al. | |
| 6,979,318 B1 | 12/2005 | McDonald et al. | |
| 7,341,571 B1 | 3/2008 | Harris et al. | |
| 7,434,326 B2 | 10/2008 | Gifford | |
| 7,503,904 B2 | 3/2009 | Choi | |
| 7,503,909 B2 | 3/2009 | Kusu et al. | |
| 7,763,043 B2 | 7/2010 | Goodin et al. | |
| 7,892,469 B2 | 2/2011 | Lim et al. | |
| 7,909,810 B2 | 3/2011 | Noone | |
| 7,951,186 B2 | 5/2011 | Eidenschink et al. | |
| 7,951,819 B2 | 5/2011 | Niculescu-Duyaz et al. | |
| 7,959,644 B2 | 6/2011 | Shriver | |
| 8,088,103 B2 | 1/2012 | Teeslink et al. | |
| 8,162,879 B2 | 4/2012 | Hattangadi et al. | |
| 8,241,241 B2 | 8/2012 | Evans et al. | |
| 8,262,611 B2 | 9/2012 | Teeslink et al. | |
| 8,419,648 B2 | 4/2013 | Corl et al. | |
| 8,430,899 B2 | 4/2013 | Dae et al. | |
| 8,499,681 B2 | 8/2013 | Kanner et al. | |
| 8,545,382 B2 | 10/2013 | Suzuki et al. | |
| 8,655,798 B2 | 2/2014 | Humphrey et al. | |
| 8,672,868 B2 | 3/2014 | Simons | |
| 8,747,358 B2 | 6/2014 | Trombley, III et al. | |
| 8,814,900 B2 | 8/2014 | Fleming, III | |
| 8,900,214 B2 | 12/2014 | Nance et al. | |
| 8,948,848 B2 | 2/2015 | Merhi | |
| 8,951,565 B2 | 2/2015 | McCarthy | |
| 9,131,874 B2 | 9/2015 | Eliason et al. | |
| D748,257 S | 1/2016 | Franklin | |
| 9,414,843 B2 | 8/2016 | Pavcnik et al. | |
| 9,474,882 B2 | 10/2016 | Franklin | |
| 9,492,084 B2 * | 11/2016 | Behar | A61B 5/0002 |
| 9,682,217 B2 | 6/2017 | Franklin et al. | |
| 9,687,333 B2 | 6/2017 | Angel et al. | |
| 10,111,669 B2 | 10/2018 | Eliason et al. | |
| 10,149,962 B2 | 12/2018 | Franklin | |
| 10,188,345 B2 * | 1/2019 | Venkatraman | A61B 5/0816 |
| 10,232,142 B2 | 3/2019 | Franklin | |
| 10,368,872 B2 | 8/2019 | Franklin | |
| 10,569,062 B2 | 2/2020 | Franklin | |
| 10,765,841 B2 * | 9/2020 | Zhadkevich | A61M 25/10184 |
| 10,806,903 B2 | 10/2020 | Franklin et al. | |
| 10,885,813 B2 | 1/2021 | Krummenacher et al. | |
| 11,013,515 B2 * | 5/2021 | Zhadkevich | A61B 17/12031 |
| 11,253,264 B2 | 2/2022 | Franklin et al. | |
| 11,311,365 B2 * | 4/2022 | Zhadkevich | A61B 17/12045 |
| 2002/0007146 A1 | 1/2002 | Omaleki et al. | |
| 2002/0062119 A1 | 5/2002 | Zadno-Azizi | |
| 2002/0193735 A1 | 12/2002 | Stiger | |
| 2003/0023200 A1 | 1/2003 | Barbut et al. | |
| 2003/0032974 A1 | 2/2003 | Leschinsky et al. | |
| 2003/0167038 A1 | 9/2003 | Yozu et al. | |
| 2004/0073162 A1 | 4/2004 | Bleam et al. | |
| 2004/0082935 A1 | 4/2004 | Lee et al. | |
| 2004/0254528 A1 | 12/2004 | Adams et al. | |
| 2005/0059931 A1 | 3/2005 | Garrison et al. | |
| 2005/0148812 A1 | 7/2005 | Nigroni et al. | |
| 2005/0261725 A1 | 11/2005 | Crawford et al. | |
| 2007/0043307 A1 | 2/2007 | Raulerson et al. | |
| 2007/0043409 A1 | 2/2007 | Brian, III et al. | |

(56) References Cited

U.S. PATENT DOCUMENTS

| | | |
|---|---|---|
| 2007/0106258 A1* | 5/2007 | Chiu .................. A61M 25/10 604/509 |
| 2007/0129466 A1 | 6/2007 | Kagawa et al. |
| 2007/0135830 A1 | 6/2007 | Schaeffer |
| 2007/0219466 A1 | 9/2007 | Tremulis et al. |
| 2007/0219488 A1 | 9/2007 | Francescatti |
| 2007/0270935 A1 | 11/2007 | Newhauser et al. |
| 2008/0027356 A1 | 1/2008 | Chen et al. |
| 2008/0051764 A1 | 2/2008 | Dent et al. |
| 2008/0082046 A1 | 4/2008 | Kato et al. |
| 2008/0082119 A1 | 4/2008 | Vitullo |
| 2008/0097300 A1 | 4/2008 | Eskaros et al. |
| 2008/0243067 A1 | 10/2008 | Rottenberg et al. |
| 2008/0243221 A1 | 10/2008 | Arcand |
| 2008/0262477 A1 | 10/2008 | Djaladat |
| 2009/0026595 A1 | 1/2009 | Kadoi |
| 2009/0062666 A1 | 3/2009 | Roteliuk |
| 2009/0171272 A1 | 7/2009 | Tegg et al. |
| 2009/0171293 A1 | 7/2009 | Yang et al. |
| 2009/0265951 A1 | 10/2009 | Black |
| 2009/0287079 A1 | 11/2009 | Shriver |
| 2009/0312807 A1 | 12/2009 | Boudreault et al. |
| 2010/0016735 A1 | 1/2010 | Harpas et al. |
| 2010/0041984 A1 | 2/2010 | Shapland et al. |
| 2010/0234915 A1 | 9/2010 | Herlich et al. |
| 2010/0262076 A1 | 10/2010 | Rowe et al. |
| 2010/0268017 A1 | 10/2010 | Siess |
| 2010/0280451 A1 | 11/2010 | Teeslink et al. |
| 2010/0292635 A1 | 11/2010 | Sundar |
| 2011/0144742 A1 | 6/2011 | Madrid et al. |
| 2011/0196412 A1 | 8/2011 | Levit et al. |
| 2011/0230821 A1 | 9/2011 | Babic |
| 2011/0295301 A1 | 12/2011 | Hoem et al. |
| 2011/0295302 A1 | 12/2011 | Mohl |
| 2011/0301630 A1 | 12/2011 | Hendriksen et al. |
| 2012/0101413 A1 | 4/2012 | Beetel et al. |
| 2012/0108979 A1 | 5/2012 | Franklin et al. |
| 2012/0109057 A1 | 5/2012 | Krolik et al. |
| 2012/0116352 A1 | 5/2012 | Rangi |
| 2012/0130359 A1 | 5/2012 | Turovskiy |
| 2012/0172911 A1 | 7/2012 | Welch |
| 2012/0209176 A1 | 8/2012 | Anderson |
| 2012/0215166 A1 | 8/2012 | Barki |
| 2012/0271231 A1 | 10/2012 | Agrawal |
| 2012/0302994 A1 | 11/2012 | Wilson et al. |
| 2013/0102926 A1 | 4/2013 | Eliason et al. |
| 2013/0102929 A1 | 4/2013 | Haight et al. |
| 2013/0172786 A1 | 7/2013 | Olson et al. |
| 2013/0190619 A1 | 7/2013 | Nudel |
| 2013/0281869 A1 | 10/2013 | Barbut et al. |
| 2013/0289607 A1 | 10/2013 | Pedersen et al. |
| 2013/0338637 A1 | 12/2013 | Fischer, Jr. et al. |
| 2014/0221898 A1 | 8/2014 | Kurrus et al. |
| 2014/0243873 A1 | 8/2014 | Franklin |
| 2014/0249504 A1 | 9/2014 | Franklin et al. |
| 2014/0316012 A1 | 10/2014 | Freyman et al. |
| 2014/0350523 A1* | 11/2014 | Dehdashtian ....... A61M 1/3666 604/509 |
| 2014/0364835 A1 | 12/2014 | Allen et al. |
| 2014/0378869 A1 | 12/2014 | Sela et al. |
| 2015/0012031 A1 | 1/2015 | Rago et al. |
| 2015/0039012 A1 | 2/2015 | Solar et al. |
| 2015/0272732 A1 | 10/2015 | Tilson et al. |
| 2015/0367098 A1 | 12/2015 | Aggerholm et al. |
| 2016/0000446 A1 | 1/2016 | Eliason et al. |
| 2016/0166197 A1* | 6/2016 | Venkatraman ....... A61B 5/0816 600/595 |
| 2016/0206798 A1 | 7/2016 | Williams et al. |
| 2016/0213893 A1 | 7/2016 | Franklin |
| 2016/0262647 A1 | 9/2016 | Berenfeld |
| 2016/0375230 A1 | 12/2016 | Lee et al. |
| 2017/0043123 A1 | 2/2017 | Franklin |
| 2017/0368313 A1 | 12/2017 | Franklin et al. |
| 2018/0236203 A1 | 8/2018 | Franklin et al. |
| 2019/0015630 A1 | 1/2019 | Franklin et al. |
| 2019/0076152 A1 | 3/2019 | Franklin et al. |
| 2019/0307462 A1 | 10/2019 | Franklin et al. |
| 2019/0378436 A1 | 12/2019 | Krummenacher et al. |
| 2020/0276419 A1 | 9/2020 | Franklin et al. |
| 2021/0290243 A1 | 9/2021 | Franklin et al. |
| 2021/0370025 A1 | 12/2021 | Pickering et al. |

FOREIGN PATENT DOCUMENTS

| | | |
|---|---|---|
| AU | 2014317859 B2 | 3/2015 |
| AU | 2015274743 B2 | 12/2015 |
| AU | 2016232781 B2 | 9/2016 |
| AU | 2017272335 B2 | 12/2017 |
| CA | 2941438 | 12/2015 |
| CA | 2980018 | 9/2016 |
| CA | 2990479 | 12/2017 |
| CN | 102740906 A | 10/2012 |
| CN | 105339035 A | 2/2016 |
| EM | 002688283-0001 | 3/2019 |
| EP | 1094861 B1 | 4/2005 |
| EP | 1658808 A1 | 5/2006 |
| EP | 1911484 A2 | 4/2008 |
| EP | 2389974 A1 | 11/2011 |
| EP | 2716323 A1 | 4/2014 |
| EP | 2837402 A2 | 2/2015 |
| EP | 3260158 B1 | 11/2018 |
| EP | 3270997 B1 | 7/2019 |
| EP | 3424552 B1 | 4/2020 |
| EP | 2961464 B1 | 5/2020 |
| EP | 3549121 B1 | 9/2021 |
| GB | 2297259 A | 7/1996 |
| GB | 90026882830001 | 4/2015 |
| IL | 240775 A | 11/2018 |
| JP | H03-198868 A | 8/1991 |
| JP | H03280962 A | 12/1991 |
| JP | H09-164208 A | 6/1997 |
| JP | H1080497 A | 3/1998 |
| JP | 2000217922 A | 8/2000 |
| JP | 2002505165 A | 2/2002 |
| JP | 2003535652 A | 12/2003 |
| JP | 200714820 A | 1/2007 |
| JP | 2008-237529 A | 10/2008 |
| JP | 2008546471 A | 12/2008 |
| JP | 2010-538797 A | 12/2010 |
| JP | 2011245300 A | 12/2011 |
| JP | 6286564 B2 | 2/2018 |
| JP | 6343009 B2 | 6/2018 |
| JP | 6343290 B2 | 6/2018 |
| JP | 6345192 B2 | 6/2018 |
| JP | 6408176 B2 | 10/2018 |
| JP | 6472536 B2 | 2/2019 |
| WO | 92/20398 | 11/1992 |
| WO | 97/13542 | 4/1997 |
| WO | 98/34670 | 8/1998 |
| WO | 1999/24105 | 5/1999 |
| WO | 99/44666 | 9/1999 |
| WO | 01/97743 A2 | 12/2001 |
| WO | 2004/049970 A2 | 6/2004 |
| WO | 2006/014631 A1 | 2/2006 |
| WO | 2006/135853 A2 | 12/2006 |
| WO | 2007/001701 A1 | 1/2007 |
| WO | 2007/022592 A1 | 3/2007 |
| WO | 2008/013441 A1 | 1/2008 |
| WO | 2009/039203 A2 | 3/2009 |
| WO | 2010/070685 A1 | 6/2010 |
| WO | 2011/133736 A2 | 10/2011 |
| WO | 2014/003809 A1 | 1/2014 |
| WO | 2014/134215 A1 | 9/2014 |
| WO | 2014/152191 A1 | 9/2014 |
| WO | 2015/006828 A1 | 1/2015 |
| WO | 2015/035393 A1 | 3/2015 |
| WO | 2015/181167 A1 | 12/2015 |
| WO | 2015/191685 A1 | 12/2015 |
| WO | 2016/145163 A1 | 9/2016 |
| WO | 2016/149653 A2 | 9/2016 |
| WO | 2016/149653 A3 | 11/2016 |

(56) References Cited

FOREIGN PATENT DOCUMENTS

| WO | 2017/210584 A1 | 12/2017 |
|---|---|---|
| WO | 2018/132623 A1 | 7/2018 |

OTHER PUBLICATIONS

Extended European Search Report dated Sep. 17, 2020 for European Application No. 18738917.6, 8 pages.
Holcomb et al., "Causes of death in US Special Operations Forces in the global war on terrorism: 2001-2004," Annals of Surgery, vol. 245, No. 6, pp. 986-991 (2007).
Sohn et al., "Demographics, Treatment, and Early Outcomes in Penetrating Vascular Combat Trauma," Arch Surg, vol. 143, No. 8, pp. 783-787 (2008).
Fenton et al., "Comparing risks of alternative medical diagnosis using Bayesian arguments," J. Biomed. Inf., vol. 43, pp. 485-495 (2010).
Patel et al., "Bayesian Designs for Device Clinical Trials," MDG Forum, Waltham, MA., Nov. 3, 2010, downloaded from web page: <http://www.cytel.com/pdfs/PatelBayes_Devices_Slides_11.18.10.pdf>.
Guidance for the Use of Bayesian Statistics in Medical Device Clinical Trials, U.S. Department of Health and Human Services, Food and Drug Administration, Center for Devices and Radiological Health, Division of Biostatistics, Office of Surveillance and Biometrics, Feb. 5, 2010.
Sandgren et al., "The Diameter of the Common Femoral Artery in Healthy Human: Influence of Sex, Age, and Body Size," Journal of Vascular Surgery, vol. 29, No. 3, pp. 503-510 (1999).
Sam II et al., "Blunt Traumatic Aortic Transection: Endoluminal Repair with Commercially Available Aortic Cuffs," Journal of Vascular Surgery, vol. 38, No. 5, pp. 1132-1135 (2003).
Detrano et al. "Bayesian Probability Analysis: A Prospective Demonstration of its Clinical Utility in Diagnosing Coronary Disease," Circulation, vol. 69, No. 3, pp. 541-547 (1984).
Office Action, dated Nov. 21, 2022, for JP Application No. JP2021-128750, 10 pages.

* cited by examiner

ENDOVASCULAR PERFUSION AUGMENTATION FOR CRITICAL CARE

CROSS-REFERENCE TO RELATED APPLICATIONS

This application is a continuation of International Patent Application No. PCT/US2018/013413, filed Jan. 11, 2018, which claims priority to U.S. Provisional Application Ser. No. 62/445,551, filed Jan. 12, 2017, the disclosures of which are herein incorporated by reference in their entirety for all purposes.

STATEMENT OF GOVERNMENT INTEREST

This invention was made with Government support under Grant No. HL108964, awarded by the National Institutes of Health (NIH). The Government has certain rights in the invention.

FIELD OF USE

The present disclosure relates generally to endovascular aortic flow regulation devices deployed within the aorta. More particularly, the invention relates to systems and methods for endovascular perfusion augmentation for critical care.

BACKGROUND

Death from the complications of shock continues to exist as a high probability in an overwhelming number of cases in both medical and surgical patients. Existing systems, medications, and procedures used to treat shock states frequently contribute to a patient's ultimate death through inability to maintain adequate oxygen delivery to vital organs. This delivery of oxygen is predicated on adequate blood perfusion to the organs. It is well recognized that without sufficient blood pressure to the heart and lungs hemodynamic collapse ensues resulting in decreased perfusion to the remaining organs and eventual death.

Restoring homeostasis for a patient in shock is difficult and labor intensive. The dynamic nature of the patient's physiology after a severe initial insult requires both medical expertise as well as continuous appraisal and modification to the care provided. Yet, for all the sophistication and innovation of modern medicine, the current "state of the art" in critical care medicine remains a fairly imprecise "one size fits all" resuscitation and critical care strategy. The resuscitation of a patients suffering from shock, whether neurogenic, hemorrhagic, hypovolemic, or septic, poses unique challenges especially during the early hours of critical care. Any episodes of hypotension can be detrimental to the patient. Older patients, as well as patients who have suffered a traumatic brain injury are especially susceptible to episodes of hypotension.

Current practice to treat shock is dependent upon the etiology, but almost all treatment algorithms include intravenous (IV) fluids or blood products and, when necessary, titration of vasoactive medications that act upon the vasculature to cause vasoconstriction and an increase in blood pressure. For example, the primary focus in hemorrhagic shock is aggressive transfusion of blood products in roughly the same amounts and composition of the blood that was lost. Likewise, in sepsis and ischemia-reperfusion injuries, resuscitation is initiated with large IV crystalloid boluses irrespective of the underlying pathophysiology. However, in these instances, and many other critical care scenarios, the doses of fluid and vasopressors are approximations and the endpoints are fairly subjective. Thus, modern shock resuscitation is still not precisely targeted towards the physiologic demands of the individual patient. This lack of precision ultimately arises from the inability to efficiently analyze the efficacy of care in real time, e.g., second-to-second and minute-to-minute, and provide rapid adjustments in response to a critically ill patient's physiology.

For example, although the nuances of treating shock are dependent upon etiology, all treatment modalities suffer from similar drawbacks. First, IV fluids are often required in large amounts early on during treatment to improve blood pressure. At times, the volume of fluid can be so great that it overwhelms the cardiovascular system resulting in pulmonary edema, ARDS, or heart failure. Therefore, although often required early on in treatment, alternative methods to remove this excess fluid are often required as soon as the patient can tolerate diuresis.

A second complication from current therapies is the secondary consequences of high doses of vasopressor medications. Vasopressors act directly on the blood vessels to increase vascular tone and improve systemic blood pressure. In the absence of a better therapeutic solution, these medications are at times necessary to improve perfusion to vital organs. However, this systemic increase in blood pressure does come at the potential cost of poor perfusion at the microvascular level. Unfortunately, due to differential responses to these medications across organs and tissue beds, unpredictable changes in regional blood flow can occur, which may ultimately have a counterproductive or detrimental effect. With high doses of these medications, certain tissues may incur permanent injury such as the distal extremities, potentially necessitating major limb amputation. In patients suffering from traumatic brain injury with increased intracranial pressure, studies in animals and in humans have demonstrated that high doses of vasopressors are often able to improve perfusion to the injured areas of the brain, but often at the expense of other regions of the brain that have such profound vasoconstriction to result in ischemic neurons.

Finally, current therapies to treat shock take time to work. These conventional therapies are frequently unable to optimize blood pressure in a timely fashion, and in many instances fail to achieve the intended target altogether. For example, modern resuscitation is limited by the latency period between an intervention and the recognition of that intervention's physiologic effect, e.g., increase in blood pressure, urine output, oxygen saturation. Boluses of IV fluids require anywhere from several minutes to an hour to be infused, and vasopressor medications often take 10-15 minutes to prepare, administer, and achieve an effect large enough to be detected by a healthcare provider at the bedside, and often must be titrated in doses over the subsequent hours. Even once working, some forms of shock are not responsive to single medications and multiple vasopressors are required to optimize blood pressure. As a result, valuable time is lost in the attempts to restore cardiovascular homeostasis and meet physiologic goals, e.g., target blood pressure or markers of end organ perfusion, resulting in exceeding acceptable limits and irreversible tissue damage.

Furthermore, these end goals of resuscitation are frequently not even achieved, despite maximal intervention with blood products, fluids, and multiple vasoactive agents. This inherent delay is compounded by the fairly crude vital sign monitoring methods and metrics that have undergone little change over the last 150 years. Therefore, conventional resuscitation and monitoring strategies not only routinely fail to achieve goal hemodynamics in a timely fashion, but frequently fail to accurately characterize and assess the adequacy of the treatment altogether. Since even short periods of ischemia can result in organ dysfunction and decreased viability, leading to increased morbidity and mortality, improved strategies are needed to optimize blood flow and pressure in a more timely and reliable fashion.

The significant advancement of endovascular technologies to treat vascular pathology and injury over the past 25 years has provided a unique set of tools and techniques to facilitate a completely different approach to resuscitation in severe shock by directly optimizing coronary, pulmonary and cerebral perfusion at the level of the aorta. By using endovascular catheters designed to impede distal blood flow strategically placed within the aorta of a patient in shock, proximal blood pressure above the balloon can be augmented by minimizing blood flow distal to the balloon. For example, Resuscitative Endovascular Balloon Occlusion of the Aorta (REBOA) is a therapy that is used in trauma patients in extremis. REBOA is an extreme version of afterload augmentation increasingly utilized by trauma providers in the setting of uncontrolled torso hemorrhage. Rather than performing an emergency department thoracotomy to cross clamp the aorta to minimize distal aortic flow, a balloon catheter is completely inflated in the aorta above the level of injury to stop flow. By completely occluding the proximal aorta with balloon catheter, REBOA instantly isolates the distribution of circulating blood to the upper torso, thereby improving proximal organ perfusion and arresting bleeding downstream. Yet, the hemodynamic augmentation of REBOA does have a significant drawback—ischemia to all tissue distal to the point of occlusion. To counter this drawback, a dynamic partial occlusion of the aorta, termed partial-REBOA (P-REBOA) has been proposed as a method of supporting perfusion to vital organs (heart, lungs, brain) while still allowing for a low rate of distal blood flow. However, the clinical utility of P-REBOA is currently limited by imprecise control of the degree of occlusion.

Another type of occlusion device is the intra-aortic balloon pump used for patients in cardiogenic shock. Intra-aortic balloon pumps create pulsatile blood flow distally in the aorta to maximize coronary circulation. A separate device termed the "neuro-flo" was briefly trialed to improve perfusion to regions of the brain during a stroke by partially occluding the aorta. However, "neuro-flo" lacks automation, and lacks an ability to change the amount of occlusion dynamically in response to patient physiology.

The current choices of endovascular compliant balloon architecture poses technical challenges for carefully regulated distal aortic flow. As an alternative to compliant balloon architectures, there exist fixed-diameter, non-compliant balloon catheter designs (e.g., ARMADA® by Abbott Laboratories Corp., North Chicago, Ill.). However, these catheters are intended and approved for vessel dilation (angioplasty), typically for narrowed vessels (e.g., atherosclerosis). Additionally, a fixed-diameter, non-compliant balloon catheter must be sized appropriately to properly occlude each patient's aorta. Consequently, although the non-compliant balloon is less susceptible to change in shape due to blood pressure spikes, the inability to change diameter outside of a narrow range impedes its ability to serve as an adaptable device to support both complete occlusion and partial occlusion. Therefore, the relatively fixed diameter of non-compliant balloon catheters limits their real-world applicability across a range of normal aortic diameters.

Current balloon technology created for complete or partial aortic occlusion to stop distal hemorrhage in the setting of trauma are unable to provide consistent titrated flow across the complete range from complete occlusion to no occlusion. The ER-REBOA catheter from PryTime Medical is a compliant balloon catheter intended to decrease hemorrhage after trauma. The ER-REBOA catheter and similar compliant balloons from other manufacturers use balloons catheters that undergo conformational changes at varying degrees of occlusion resulting in non-predictable changes in aortic flow with small changes in balloon cather volume.

Other efforts have been directed to development of potential alternative methods of providing aortic occlusion. For example, Barbut et al., U.S. Pat. No. 6,743,196, issued Jun. 1, 2004, describes a plurality of approaches to support aortic occlusion. Each approach described in Barbut et al. includes a catheter having a distally mounted constricting mechanism. Each constrictor is collapsed to facilitate insertion and then expanded once inserted to obstruct blood flow. Barbut et al. describes a constrictor comprising an outer conical shell and an inner conical shell, each having a distal open base and proximal apex. The outer shell further includes a pre-shaped ring to facilitate expansion. Both shells include ports or openings. Flow through the mechanism is controlled by rotating the inner conical shell such that the ports of each shell communicate.

More recently, VanCamp et al, in U.S. Pat. No. 7,927,346, issued Apr. 19, 2011, describes a device to provide temporary partial aortic occlusion to achieve diversion of blood flow to the brain in patients suffering from cerebral ischemia. The primary thrust of the VanCamp et al. invention is the provision of an blood flow regulation device that does not require fluoroscopy to ensure proper placement. VanCamp's device includes an expandable frame with a planar membrane mounted on a first portion of the frame to occlude blood flow. In one embodiment disclosed in VanCamp et al., the membrane includes a fixed size opening in the center of the planar membrane to allow some blood to flow through the opening. Alternatively, VanCamp also discloses that the membrane itself may be somewhat permeable to blood flow to allow some flow. However, VanCamp is unable to provide variable control of blood flow during use.

In addition, Franklin et al, in PCT Pat. Appl. Pub. No. WO/2016149653A2, published Sep. 22, 2016, describes an occlusion catheter system and vascular pre-conditioning to mitigate ischemia before, during and/or after a vascular occlusion procedure.

Medications including vasoactive medications and intravenous fluids require time to improve physiology once physiologic derangement is recognized. For example, vasoactive medications must circulate throughout the vasculature and act through intracellular mechanisms to result in vascular constriction. These changes can take seconds, to minutes, or even hours to take effect depending upon the medication used and the underlying physiology. This time can be detrimental if the state of shock is severe. The use of an endovascular device as described in these claims allows for immediate augmentation of physiology once inappropriate physiology is identified. Automation of an endovascular perfusion augmentation device allows this to be dynamic, with continuous changes in the device on a second by second time frame to allow continuous stable physiology proximal to the device.

In light of the aforementioned considerations and limitations of existing and proposed devices, there exists an urgent and unmet need for a viable solution to allow a physician to address shock and carefully regulate blood flow in the aorta to augment proximal blood pressure. The ability to rapidly deliver effective blood pressure and blood flow to the heart, lungs and brain in shock states without using high amounts of blood pressure medications and IV fluids will save innumerable lives.

SUMMARY

The present disclosure overcomes the drawbacks of previously described systems by providing an automated endovascular perfusion augmentation system. Recent translational experiments have demonstrated that incorporating automation to precisely control partial aortic occlusion allows for distal aortic flow that can be finely titrated in response to dynamic changes in blood pressure. While initially applied to settings of ongoing hemorrhagic shock, it was posited that lesser degrees of partial aortic occlusion may optimize cardiac performance in any type of shock by instant and dynamic changes in aortic afterload in a way that IV fluids and medications cannot.

Endovascular Perfusion Augmentation for Critical Care (EPACC) directly addresses all of the above limitations of current therapies for shock in many of its forms. Using automated devices to carefully control an endovascular aortic balloon catheter, EPACC provides small amounts of blood pressure support to vascular beds above the balloon while permitting continued perfusion distal to the catheter balloon. The concept of EPACC, in contrast to techniques such as REBOA, works with only partial occlusion of the aorta. REBOA maximizes proximal perfusion by completely occluding the aorta, at the expense of progressive ischemic injury to distal tissues. In contrast, EPACC only partially occludes the aorta, resulting in a more physiologic augmentation of proximal blood pressure. By placing the balloon at different levels within the aorta, the practitioner can select which distal capillary beds are exposed to decreased flow. Deployment of EPACC in the descending thoracic aorta results in mild reduction in blood flow to the mesentery, kidneys, liver, and extremities. In contrast, deployment at the aortic bifurcation only results in potential reduction in blood flow to the pelvis and limbs. Since aortic blood flow often exceeds what is physiologically required, minimal to moderate aortic blood flow restriction only results in minimal ischemia. This tradeoff between proximal blood pressure augmentation and distal ischemia is dependent upon the extent of shock as well as underlying patient's physiology.

The use of EPACC could be broad to treat a wide range of shock states. Initially EPACC was designed to treat shock following trauma, specifically the ischemia-reperfusion injury that is common following REBOA and aortic cross clamping procedures. EPACC is just as viable though for treating hemorrhagic shock when sufficient blood products are not available, or septic shock to decrease the amount of IV fluids and vasopressors required for treatment. The ability of EPACC to be automated to respond dynamically to any physiologic measure make it a viable technology to maximize cerebral perfusion in patients suffering from traumatic brain injuries.

The system may include a catheter having a proximal end portion and a distal end portion, wherein the distal end portion may be placed within an aorta of a patient. The system may further include an expandable aortic blood flow regulation device disposed on the distal end portion of the catheter for placement within the aorta. The expandable aortic blood flow regulation device may expand to restrict blood flow through the aorta and to contract. For example, the expandable aortic blood flow regulation device may be a balloon that may be inflated to expand to partially occlude blood flow through the aorta. In another embodiment, the expandable aortic blood flow regulation device may include a balloon that may be inflated to occlude blood flow through the aorta, and one or more wires that surround the balloon. Accordingly, the one or more wires may be tightened to indent the balloon to permit blood flow around the balloon. In another embodiment, the expandable aortic blood flow regulation device may include a wire framework that may radially expand or contract from a center axis of the catheter, and an blood flow regulation sail comprising a thin membrane that surrounds a portion of the wire framework. In another embodiment, the expandable aortic blood flow regulation device may include a non-compliant balloon having one or more windows, and a compliant balloon enclosed within the non-compliant balloon.

In one embodiment, the system may further comprise a second expandable aortic blood flow regulation device disposed on the distal end portion of the catheter proximal to the expandable aortic blood flow regulation device for placement within the aorta. The second expandable aortic blood flow regulation device may be coupled to the catheter controller unit and may expand to partially occlude blood flow through the aorta and to contract. The expandable aortic blood flow regulation device and the second expandable aortic blood flow regulation device may be spaced apart such that the expandable aortic blood flow regulation device is placed in a zone of the aorta, and the second expandable aortic blood flow regulation device is placed in a different zone of the aorta.

The system may further include a catheter controller unit coupled to the proximal end portion of the catheter. The catheter controller unit may cause the expandable aortic blood flow regulation device to expand and contract in the aorta. When the expandable aortic blood flow regulation device is a balloon that may be inflated to expand to partially occlude blood flow through the aorta, e.g., a balloon catheter, the catheter controller unit may include a syringe pump that may inflate or deflate the balloon to adjust the amount of blood flow through the aorta if the measured physiological information falls outside the target physiological range. When the expandable aortic blood flow regulation device is a balloon having one or more wires surrounding the balloon, e.g., a wire-over-balloon catheter, the catheter controller unit may include a syringe pump that may inflate or deflate the balloon, and a stepper motor or a motorized arm that may shorten or lengthen the one or more wires to tighten or loosen the one or more wires surrounding the balloon to adjust the amount of blood flow through the aorta if the measured physiological information falls outside the target physiological range. When the expandable aortic blood flow regulation device is a wire framework having an blood flow regulation sail, e.g., an intra-aortic sail catheter, the catheter controller unit may include a stepper motor or a motorized arm that may shorten or lengthen the wire framework to radially expand or contract the blood flow regulation sail to adjust the amount of blood flow through the aorta if the measured physiological information falls outside the target physiological range. When the expandable aortic blood flow regulation device is a compliant balloon enclosed within a non-compliant balloon, the catheter controller unit may be a syringe pump that may inflate or deflate the compliant balloon such that the compliant balloon is extruded through the one or more windows of the non-compliant balloon to adjust the amount of blood flow through the aorta if the measured physiological information falls outside the target physiological range.

The system may further include one or more sensors for measuring physiological information indicative of blood flow through the aorta. For example, one of the one or more sensors may be disposed on the catheter distal to the expandable aortic blood flow regulation device and may measure physiological information indicative of blood pressure in the aorta distal to the expandable aortic blood flow regulation device, and/or one of the one or more sensors may be disposed on the catheter proximal to the expandable aortic blood flow regulation device and may measure physiological information indicative of blood pressure in the aorta proximal to the expandable aortic blood flow regulation device. The one or more sensors may measure physiological information indicative of blood flow through the aorta including at least one of heart rate, respiratory rate, aortic blood flow proximal or distal to the expandable aortic blood flow regulation device, blood temperature, pressure within the expandable aortic blood flow regulation device, cardiac output of the patient, carotid blood flow, pulmonary pressures, peripheral vascular resistance, or intracranial pressure. Additionally, the one or more sensors may measure physiological information indicative of blood flow through the aorta by measuring at least one of lactate level, cortisol level, reactive oxygen species level, or pH, of a fluid of the patient. In an embodiment where two expandable aortic blood flow regulation devices are utilized, at least one of the one or more sensors may be positioned distal to the expandable aortic blood flow regulation device, in between the expandable aortic blood flow regulation device and the second expandable aortic blood flow regulation device, or proximal to the second expandable aortic blood flow regulation device.

The system may further include a non-transitory computer readable media having instructions stored thereon, wherein the instructions, when executed by a processor coupled to the one or more sensors, cause the processor to compare the measured physiological information with a target physiological range such that the catheter controller unit automatically adjusts expansion and contraction of the expandable aortic blood flow regulation device to adjust an amount of blood flow through the aorta if the measured physiological information falls outside the target physiological range.

In one embodiment, the system may further comprise an external central processing unit operatively coupled to the one or more sensors and the catheter controller unit. The external central processing unit may include the processor and transmit information indicative of whether the measured physiological information falls outside the target physiological range to the catheter controller unit. For example, the external central processing unit may transmit the information to the catheter controller unit via at least one of WiFi, Bluetooth, Wixel-based communication, or cellular communication.

In one embodiment, the system may further comprise an automated pump for delivering intravenous medication to the patient, wherein the instructions, when executed by the processor coupled to the one or more sensors, cause the processor to compare the measured physiological information with a target physiological range such that the automated pump delivers intravenous medications to the patient to modulate patient physiology based on the comparison.

In one embodiment, the system may further comprise an automated pump for delivering intravenous fluids and blood products to the patient, wherein the instructions, when executed by the processor coupled to the one or more sensors, cause the processor to compare the measured physiological information with a target physiological range such that the automated pump delivers intravenous fluids or blood products to the patient to modulate patient physiology based on the comparison.

In accordance with yet another aspect of the present disclosure, a method for automatically, dynamically regulating the degree of aortic blood flow regulation for endovascular perfusion augmentation. The method may include introducing a distal end portion of a catheter having an expandable aortic blood flow regulation device within an aorta of a patient, expanding the expandable aortic blood flow regulation device to partially occlude blood flow through the aorta, measuring physiological information indicative of blood flow through the aorta via one or more sensors, comparing the measured physiological information with a target physiological range, and adjusting expansion and contraction of the expandable aortic blood flow regulation device to adjust an amount of blood flow through the aorta if the measured physiological information falls outside the target physiological range.

In one embodiment, the catheter further includes a second expandable aortic blood flow regulation device disposed on the distal end portion of the catheter proximal to the expandable aortic blood flow regulation device for placement within an aorta or distal artery of a patient. The second expandable aortic blood flow regulation device may expand to partially occlude blood flow, and the expandable aortic blood flow regulation device may be placed in a zone of the aorta, while the second expandable aortic blood flow regulation device may be placed in a different zone of the aorta or in blood vessels more distal to the aorta. Accordingly, the method may further include expanding the second expandable aortic blood flow regulation device to occlude blood flow, and expanding or contracting the second expandable aortic blood flow regulation device to adjust the amount of blood flow if the measured physiological information falls outside the target physiological range.

DETAILED DESCRIPTION

Endovascular Perfusion Augmentation for Critical Care (EPACC) is a novel therapeutic platform to mechanically and pharmacologically augment blood pressure of patients with critical illness. EPACC is achieved via a system comprising a series of endovascular devices, controller units for those devices, and complex algorithms capable of real-time changes in the EPACC devices in response to patient physiology. The ability of EPACC to be automated to respond dynamically to any physiologic measure makes it a viable technology to maximize perfusion in multiple shock states. In accordance with the principles of the present disclosure, EPACC is just as viable though for treating hemorrhagic shock when sufficient blood products are not available, or septic shock to decrease the amount of IV fluids and vasopressors required for treatment, or neurogenic shock in the setting of traumatic brain injury or intracerebral hemorrhage.

Figure 1:
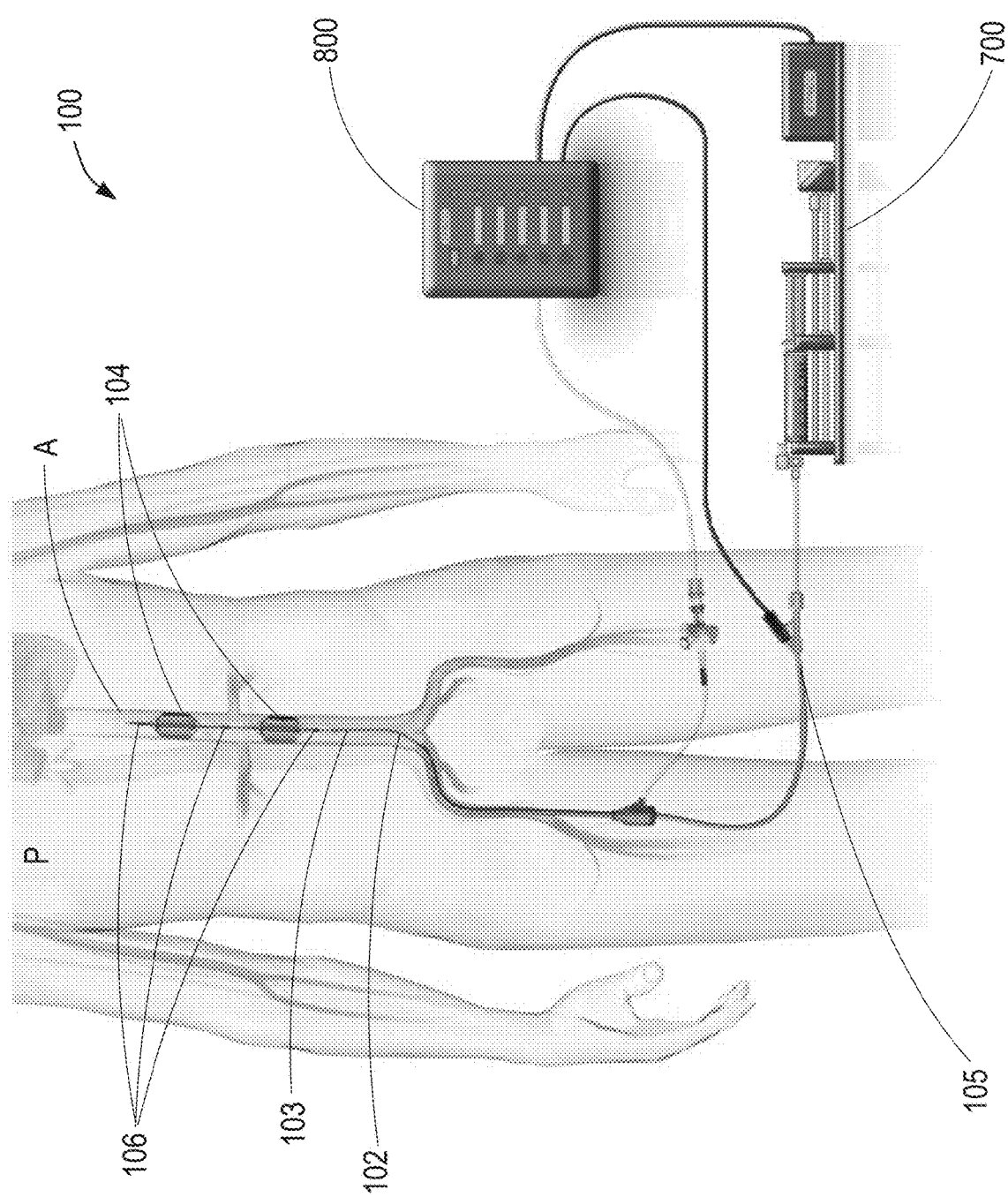
FIG. 1 illustrates an exemplary automated endovascular perfusion augmentation system constructed in accordance with the principles of the present disclosure.

Referring to FIG. 1, an exemplary automated endovascular perfusion augmentation system constructed in accordance with the principles of the present disclosure is described. In FIG. 1, the components of automated endovascular perfusion augmentation system 100 are not depicted to scale on either a relative or absolute basis. System 100 comprises catheter 102 coupled to catheter controller unit 700 and external processing unit 800 (optional). Catheter 102 includes distal end 103 and proximal end 105, and is sized and shaped for placement within aorta A of patient P. Catheter 102 may be any catheter well-known in the art, having a length sufficiently long such that catheter 102 may be inserted into a patient via the femoral artery or radial artery, and extend through the patient's vasculature into the aorta. Catheter 102 may also include expandable blood flow regulation device 104 and sensors 106 disposed at distal end 103.

Unlike current intra-aortic catheters, catheter 102 may be designed to be used for EPACC. For example, expandable blood flow regulation device 104 of catheter 102 may be designed to expand and contract, e.g., inflate and deflate, without undergoing morphological changes over time.

Expandable blood flow regulation device 104 may be strategically placed within the aorta of a patient in shock and is designed to regulate blood flow through the aorta of the patient such that blood flow distal to expandable blood flow regulation device 104 may be impeded to augment blood pressure proximal to expandable blood flow regulation device 104. Expandable blood flow regulation device 104 may comprise two expandable blood flow regulation devices disposed in series at distal end 103 of catheter 102. Accordingly, the expandable blood flow regulation devices may be spaced apart such that one expandable blood flow regulation device is placed in a specified zone of the aorta, and the second expandable blood flow regulation device is placed in a different specified zone of the aorta. For example, one expandable blood flow regulation device may be placed in zone 1 of the aorta, while the second expandable blood flow regulation device is placed in zone 3 of the aorta. As such, by placing the expandable blood flow regulation devices at different levels within the aorta, the practitioner may select which distal capillary beds are exposed to decreased flow. For example, placing and expanding an expandable blood flow regulation device in zone 1 of the aorta results in mild reduction in blood flow to the mesentery, kidneys, liver, and extremities of the patient. In contrast, placing and expanding an expandable blood flow regulation device results in potential reduction in blood flow to the pelvis and limbs of the patient. Expandable blood flow regulation device 104 may comprise various balloons and/or alternative device designs as described in further detail below.

As expandable blood flow regulation device 104 only partially restricts blood flow in the aorta, more physiologic augmentation of proximal blood pressure may result, while simultaneously optimizing blood flow to downstream organs and tissue beds. Since aortic blood flow is greater overall than is physiologically required in the majority of cases for patient's in shock, minimal-to-moderate occlusion results in only minimal ischemia. This tradeoff between proximal blood pressure augmentation and distal ischemia is dependent upon the extent of shock as well as the patient's underlying physiology.

Sensors 106 may measure physiological information indicative of blood flow through the aorta to determine the patient's underlying physiology. For example, sensors 106 may measure physiological parameters including, but not limited to, heart rate, respiratory rate, blood pressure proximal or distal or in between the two expandable blood flow regulation devices, aortic blood flow proximal or distal or in between the two expandable blood flow regulation devices, blood temperature, pressure within the expandable blood flow regulation device, cardiac output of the patient, carotid blood flow, pulmonary pressures, peripheral vascular resistance, or intracranial pressure. Sensors 106 may include one or more sensors. For example, as shown in FIG. 1, sensors 106 comprise three sensors, and may be positioned along catheter 102 distal to the expandable blood flow regulation device, in between the expandable blood flow regulation device and the second expandable blood flow regulation device, and/or proximal to the second expandable blood flow regulation device.

Sensors 106 may record data indicative of the measured physiological information either through analog or digital mechanisms. This data may then be used to determine whether more or less restriction of aortic blood flow is required to maximize vital organ perfusion via automated augmentation of blood pressure, as described in further detail below.

Patient physiology may also be monitored via real-time and intermittent measures of compounds with in the patient's blood, serum, urine, or saliva, e.g., levels of lactate, levels of cortisol, levels of reactive oxygen species, the pH of the fluid, as well as other commonly used patient physiology markers.

Catheter controller unit 700 may be coupled to proximal end 105 of catheter 102. Catheter controller unit 700 may receive the data indicative of the measured physiological information from sensors 106, and determine whether the measured physiological information is within a predetermined target physiological range. Catheter controller unit 700 may also be coupled to expandable blood flow regulation device 104 such that catheter controller unit 700 automatically adjusts expansion and contraction of expandable blood flow regulation device 104 to adjust the amount of blood flow through the aorta if the measured physiological information falls outside the target physiological range as described in further detail below.

In one embodiment, system 100 includes external central processing unit 800. External central processing unit 800 may be operatively coupled to sensors 106 and catheter controller unit 700 such that external central processing unit 800 may receive the data indicative of the measured physiological information from sensors 106, determine whether the measured physiological information is within a predetermined target physiological range, calculate the amount of change of size of expandable blood flow regulation device 104 to bring the patient physiology within the target physiological range, and transmit information indicative of whether the measured physiological information falls outside the target physiological range to central processing unit 800 as described in further detail below. Accordingly, catheter controller unit 700 automatically adjusts expansion and contraction of expandable blood flow regulation device 104 to adjust the amount of blood flow through the aorta based on the information received from external central processing unit 800.

Figure 2A:
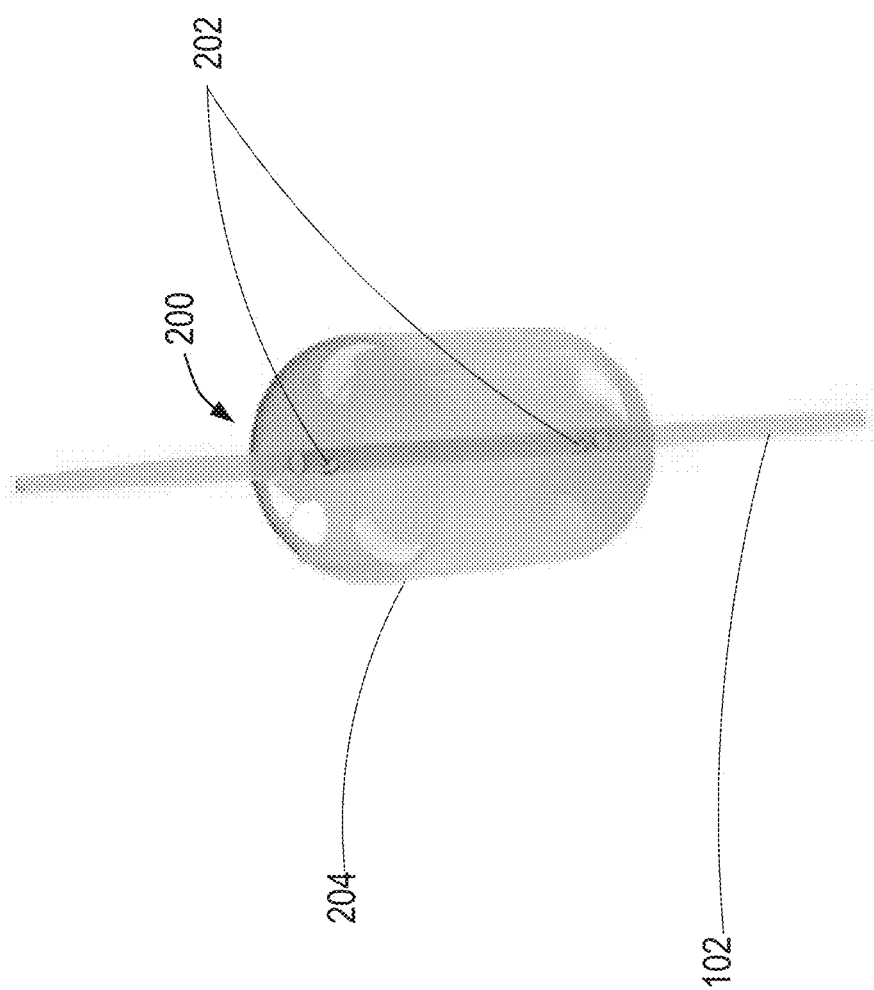
FIG. 2A illustrates a balloon catheter constructed in accordance with the principles of the present disclosure.

Referring to FIG. 2A, a balloon catheter constructed in accordance with the principles of the present disclosure is described. As shown in FIG. 2A, expandable blood flow regulation device 104 of FIG. 1 may comprise balloon catheter 200. Balloon catheter 200 comprises balloon 204 positioned at the distal end of catheter 102. Balloon 204 is designed to be inflated to a carefully titrated balloon volume to regulate blood flow in the aorta. For example, an incompressible fluid may be introduced into balloon 204 through a lumen of catheter 102 via exit ports 202 such that balloon 204 may maintain the carefully titrated balloon volume. Balloon 204 may be made of a suitable membrane that will prevent diffusion of the inflation fluid across the membrane and into the vasculature of the patient. The membrane may also be designed to inflate and deflate without undergoing morphological changes over time.

Figure 2B:
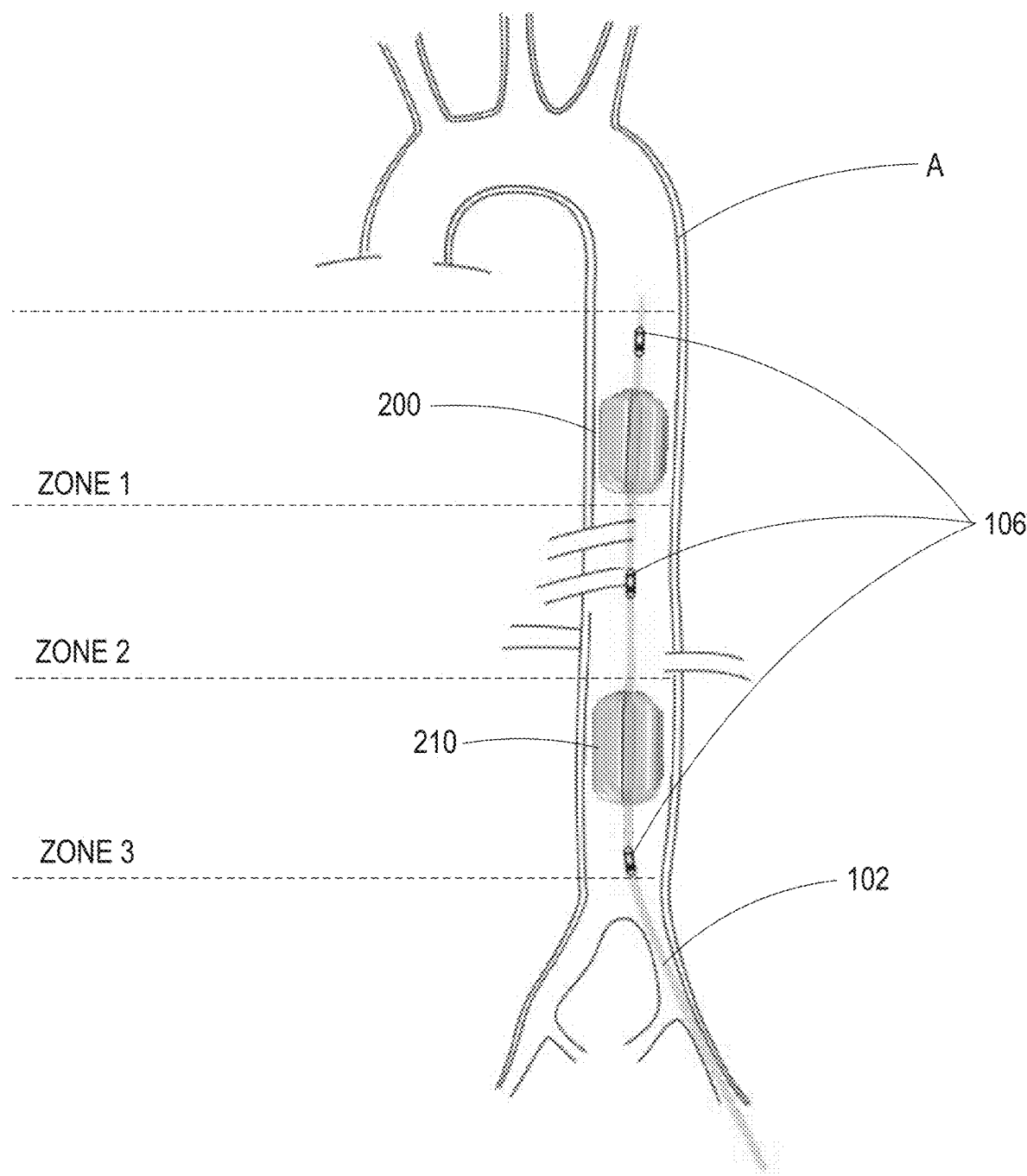
FIG. 2B shows the balloon catheter of FIG. 2A placed in series within an aorta of a patient.

As shown in FIG. 2B, balloon catheter 200 may be placed within aorta A of the patient in series with additional balloon catheter 210. Balloon catheter 210 may be constructed similarly to balloon catheter 200. Balloon catheter 200 and balloon catheter 210 may be individually inflated and deflated such that each balloon catheter maintains its own allocated carefully titrated balloon volume. Balloon catheter 200 and balloon catheter 210 may be spaced apart along the distal end of catheter 102 such that balloon catheter 200 is placed within, e.g., zone 1 of the aorta, and balloon catheter 210 is placed within, e.g., zone 3 of the aorta. This allows for blood pressure to be regulated above balloon catheter 200 in zone 1 and simultaneously above balloon catheter 210 in zone 2. As such, catheter 102 may selectively normalize perfusion to critical organs while allowing regionalized hypoperfusion to less critical organs and extremities for defined time periods. As shown in FIG. 2B, sensors 106 may comprise three sensors, e.g., solid-state pressure sensors or pressure monitoring ports, positioned above balloon catheter 200 and above and below balloon catheter 210 to allow pressure monitoring in all three zones of the aorta. As will be understood by one skilled in the art, a single balloon catheter or more than two balloon catheters may be placed within the aorta for EPACC.

Figure 3B:
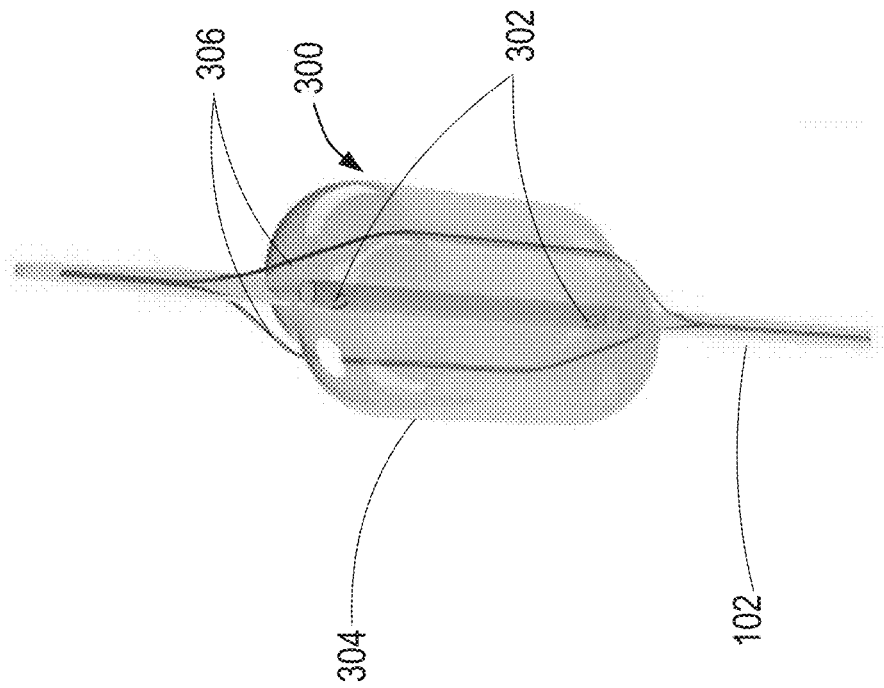
FIG. 3B illustrates the wire-over-balloon catheter of FIG. 3A wherein the wires are tightened to indent the balloon.
Figure 3A:
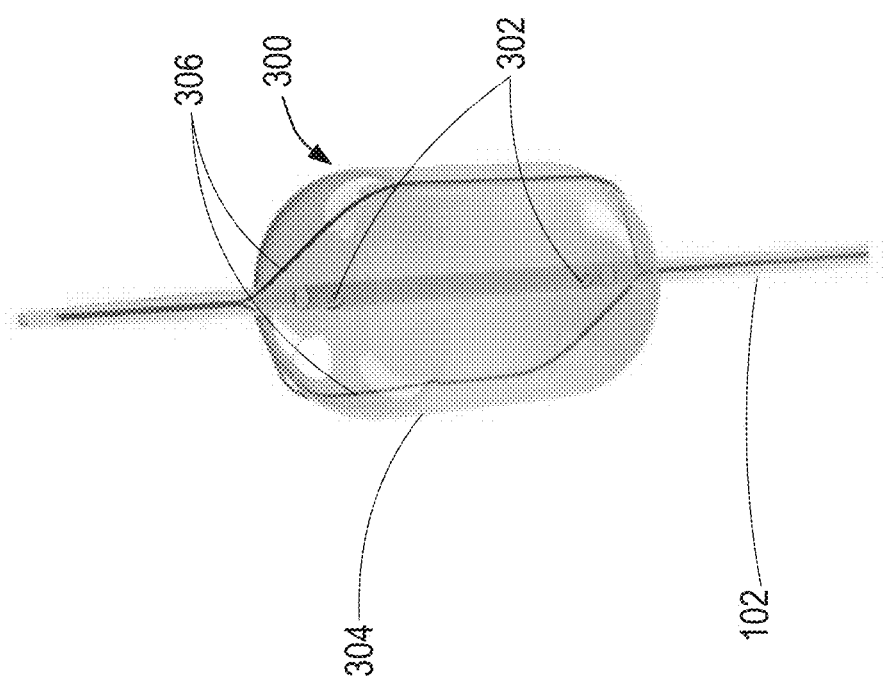
FIG. 3A illustrates a wire-over-balloon catheter having two wires.

Referring now to FIGS. 3A and 3B, an exemplary wire-over-balloon catheter is described. As shown in 3A and 3B, expandable blood flow regulation device 104 of FIG. 1 may comprise wire-over-balloon catheter 300. Wire-over-balloon catheter 300 comprises balloon 304 positioned at the distal end of catheter 102, and two wires 306 externally surrounding balloon 304. As shown in FIG. 3A, balloon 304 is designed to be inflated to fully occlude the aorta. For example, an incompressible fluid may be introduced into balloon 304 through a lumen of catheter 102 via exit ports 302 such that balloon 304 may maintain the inflated balloon volume. Balloon 304 may be made of a suitable membrane that will prevent diffusion of the inflation fluid across the membrane and into the vasculature of the patient. The membrane may also be designed to inflate and deflate without undergoing morphological changes over time.

Wires 306 may be fixed to a point along catheter 102 distal to balloon 304, traverse over balloon 304 along the longitudinal axis of balloon 304, and extend through a lumen of catheter 102 to a fixed point proximal to balloon 304. As such, catheter 102 may comprise separate lumens for receiving wires 306 and for inflating balloon 304 as described above. Wires 306 may surround balloon 304 such that wires 306 contact the wall of the aorta when balloon 304 is fully inflated. As shown in FIG. 3B, wires 306 may be immediately tightened to indent balloon 304 and create a gap between the wall of the aorta and the outer surface of balloon 304, such that the tension of wires 306 and the degree of deformation of balloon 304 correspond with the amount of blood flow past the balloon within the aorta. The degree of deformation of balloon 304 may also depend on the size of wires 306, e.g., a larger wire will result in a larger indentation.

Figure 4B:
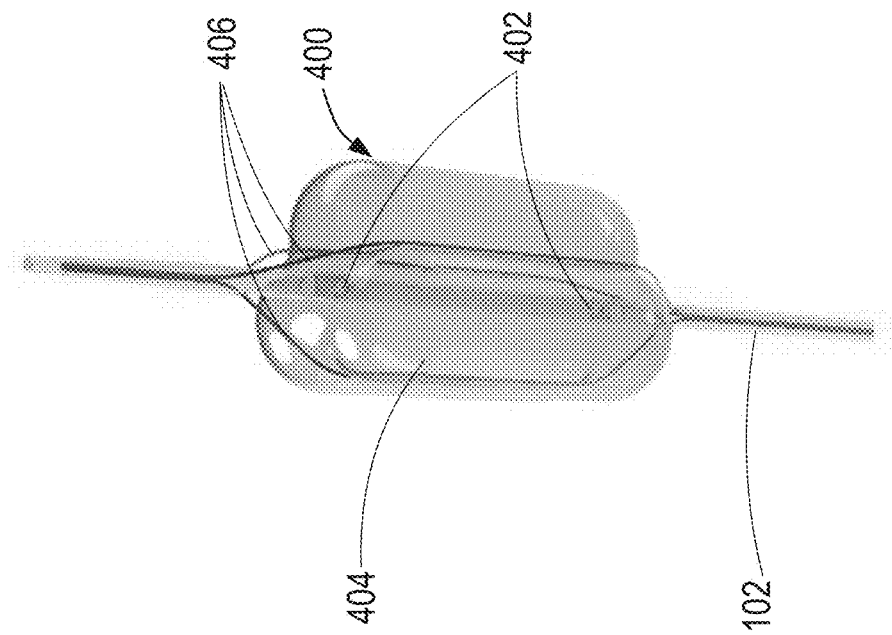
FIG. 4B illustrates the wire-over-balloon catheter of FIG. 4A wherein the wires are tightened to indent the balloon.
Figure 4A:
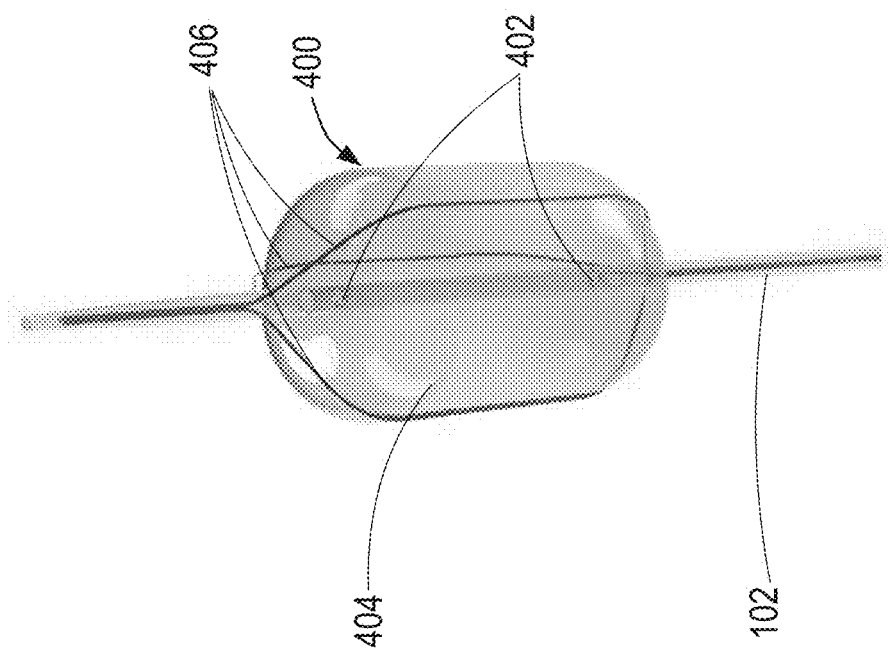
FIG. 4A illustrates a wire-over-balloon catheter having three wires.

Referring now to FIGS. 4A and 4B, another exemplary wire-over-balloon catheter is described. As shown in FIGS. 4A and 4B, expandable blood flow regulation device 104 of FIG. 1 may comprise wire-over-balloon catheter 400. Wire-over-balloon catheter 400 is constructed similarly to wire-over-balloon catheter 300 of FIGS. 3A and 3B. For example, wire-over-balloon catheter 400 comprises balloon 404 positioned at the distal end of catheter 102, and may be inflated with an incompressible fluid via exit ports 402 of catheter 102 to fully occlude the aorta. However, wire-over-balloon catheter 400 comprises three wires 406 externally surrounding balloon 404. As shown in FIG. 4B, wires 406 may be immediately tightened to indent balloon 404 and create a gap between the wall of the aorta and the outer surface of balloon 404, such that the tension of wires 406 and the degree of deformation of balloon 404 correspond with the amount of blood flow past the balloon within the aorta. As will be understood by one of ordinary skill in the art, a single wire or more than three wires may be used in a wire-over-balloon catheter. Further, the wires may surround the balloon in a manner other than along the longitudinal axis of the balloon such that the wires indent the balloon to permit blood flow past the balloon based on the degree of indentation of the balloon by the wires.

Figure 4C:
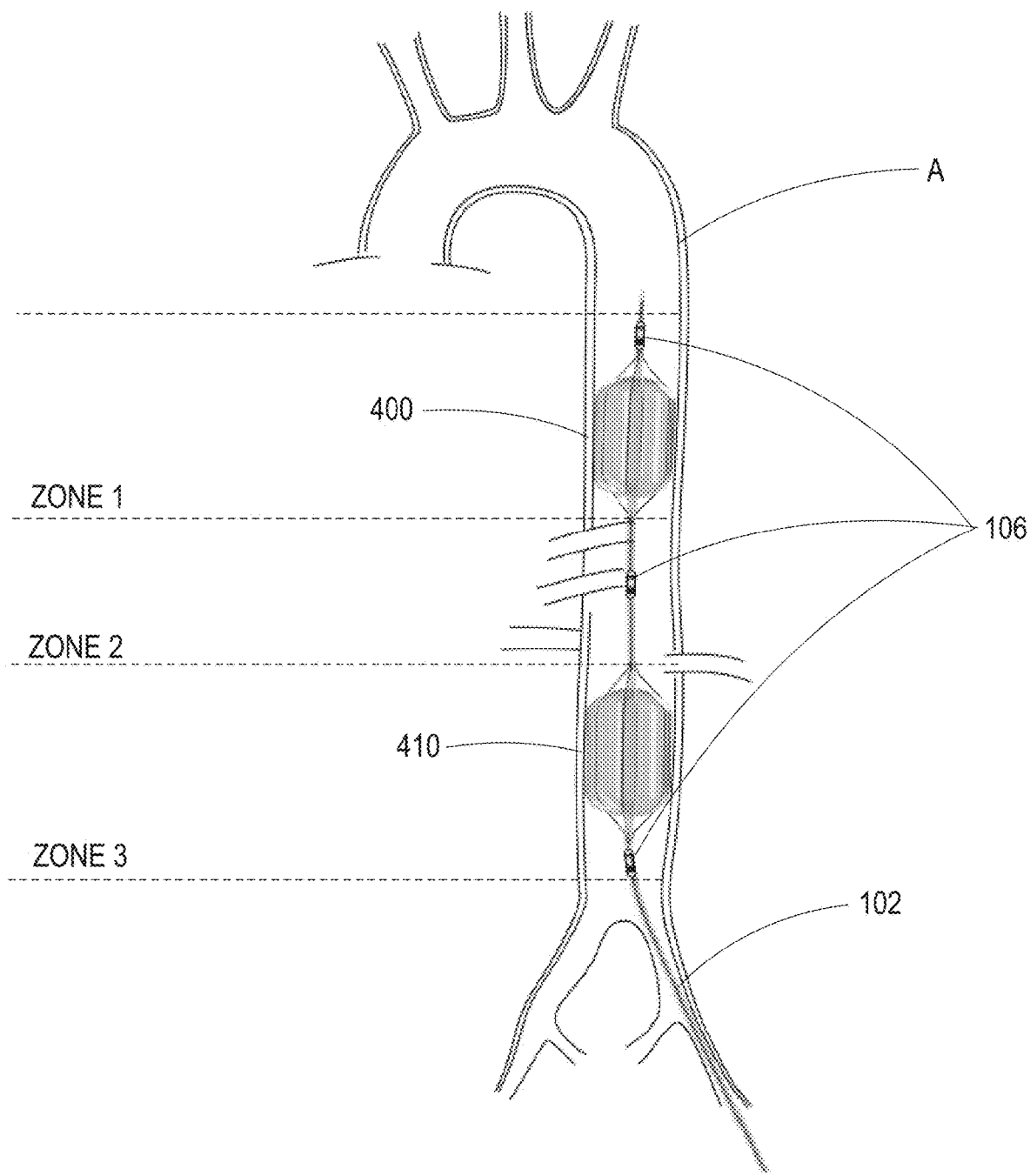
FIG. 4C shows the wire-over-balloon catheter of FIG. 4B placed in series within an aorta of a patient.

As shown in FIG. 4C, wire-over-balloon catheter 400 may be placed within aorta A of the patient in series with additional wire-over-balloon catheter 410. Wire-over-balloon catheter 410 may be constructed similarly to wire-over-balloon catheter 400. The wires of wire-over-balloon catheter 400 and wire-over-balloon catheter 410 may be individually tightened and loosened such that each wireover-balloon catheter maintains its own carefully allocated degree of indentation. Wire-over-balloon catheter 400 and wire-over-balloon catheter 410 may be spaced apart along the distal end of catheter 102 such that wire-over-balloon catheter 400 is placed within, e.g., zone 1 of the aorta, and wire-over-balloon catheter 410 is placed within, e.g., zone 3 of the aorta. This allows for blood pressure to be regulated above wire-over-balloon catheter 400 in zone 1 and simultaneously above wire-over-balloon catheter 410 in zone 2. As such, catheter 102 may selectively normalize perfusion to critical organs while allowing regionalized hypoperfusion to less critical organs and extremities for defined time periods. As shown in FIG. 4C, sensors 106 may comprise three sensors, e.g., solid-state pressure sensors or pressure monitoring ports, positioned above wire-over-balloon catheter 400 and above and below wire-over-balloon catheter 410 to allow pressure monitoring in all three zones of the aorta. As will be understood by one skilled in the art, a single wire-over-balloon catheter or more than two wire-over-balloon catheters may be placed within the aorta for EPACC.

Figure 5A:
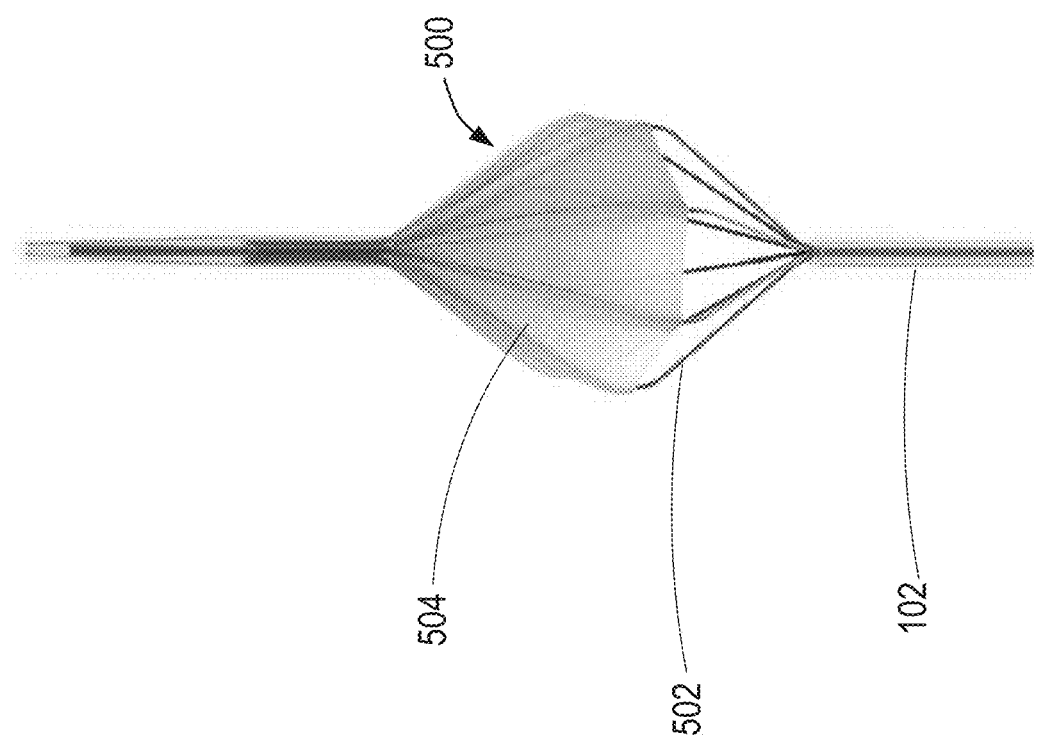
FIG. 5A illustrates an intra-aortic sail catheter constructed in accordance with the principles of the present disclosure.

Referring now to FIG. 5A, an intra-aortic sail catheter constructed in accordance with the principles of the present disclosure is described. As shown in FIG. 5A, expandable blood flow regulation device 104 of FIG. 1 may comprise intra-aortic sail catheter 500. Intra-aortic sail catheter 500 may be constructed as disclosed by Williams et al., U.S. Patent Application Publication No. 2016/0206798, published Jul. 21, 2016, which is incorporated by reference herein in its entirety. For example, intra-aortic sail catheter 500 comprises wire framework 502 and thin membrane 504 positioned at the distal end of catheter 102, wherein membrane 504 surrounds a portion of wire framework 502. Wire framework 502 comprises a plurality of wires that may be fixed to a point along catheter 102 distal to membrane 504, and extend through a lumen of catheter 102 to a fixed point proximal to membrane 504. The portion of the wires of wire framework 502 that is surrounded by membrane 502 may expand radially from the longitudinal axis of intra-aortic sail catheter 500. The wires of wire framework 502 may be expand radially such that the wires are equally spaced apart circumferentially in the expanded position. Accordingly, as wire framework 502 expands radially, membrane 504 expands creating a sail within the aorta, such that the tension of wire framework 502 and the degree of expansion of membrane 504 correspond with the amount of blood flow past the intra-aortic sail within the aorta.

Figure 5B:
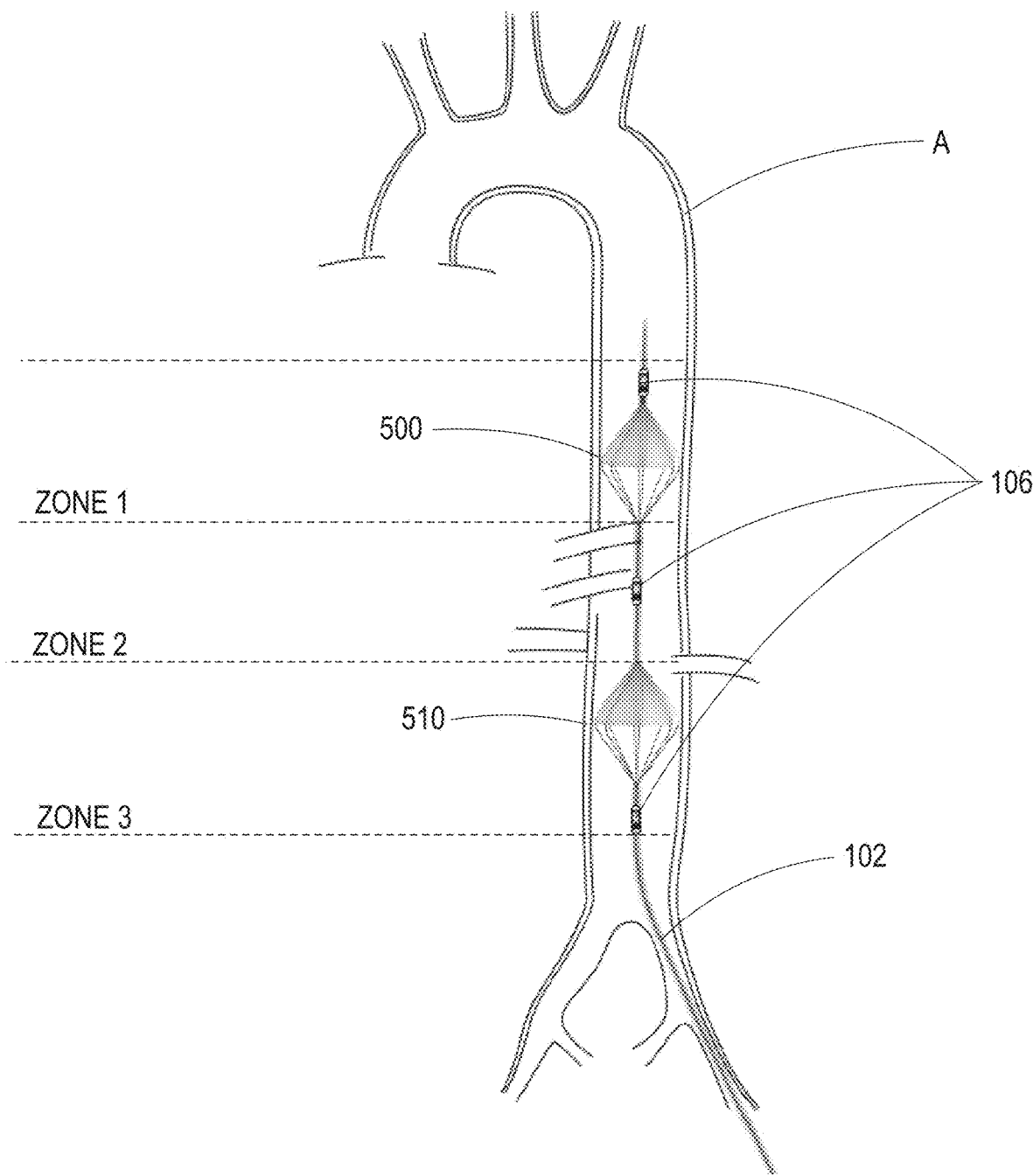
FIG. 5B shows the intra-aortic sail catheter of FIG. 5A placed in series within an aorta of a patient.

As shown in FIG. 5B, intra-aortic sail catheter 500 may be placed within aorta A of the patient in series with additional intra-aortic sail catheter 510. Intra-aortic sail catheter 510 may be constructed similarly to intra-aortic sail catheter 500. The wire frameworks of intra-aortic sail catheter 500 and intra-aortic sail catheter 510 may be individually tightened and loosened such that each intra-aortic sail catheter maintains its own carefully allocated degree of aortic occlusion. Intra-aortic sail catheter 500 and intra-aortic sail catheter 510 may be spaced apart along the distal end of catheter 102 such that intra-aortic sail catheter 500 is placed within, e.g., zone 1 of the aorta, and intra-aortic sail catheter 510 is placed within, e.g., zone 3 of the aorta. This allows for blood pressure to be regulated above intra-aortic sail catheter 500 in zone 1 and simultaneously above intra-aortic sail catheter 510 in zone 2. As such, catheter 102 may selectively normalize perfusion to critical organs while allowing regionalized hypoperfusion to less critical organs and extremities for defined time periods. As shown in FIG. 5B, sensors 106 may comprise three sensors, e.g., solid-state pressure sensors or pressure monitoring ports, positioned above intra-aortic sail catheter 500 and above and below intra-aortic sail catheter 510 to allow pressure monitoring in all three zones of the aorta. As will be understood by one skilled in the art, a single intra-aortic sail catheter or more than two intra-aortic sail catheters may be placed within the aorta for EPACC.

Figure 6:
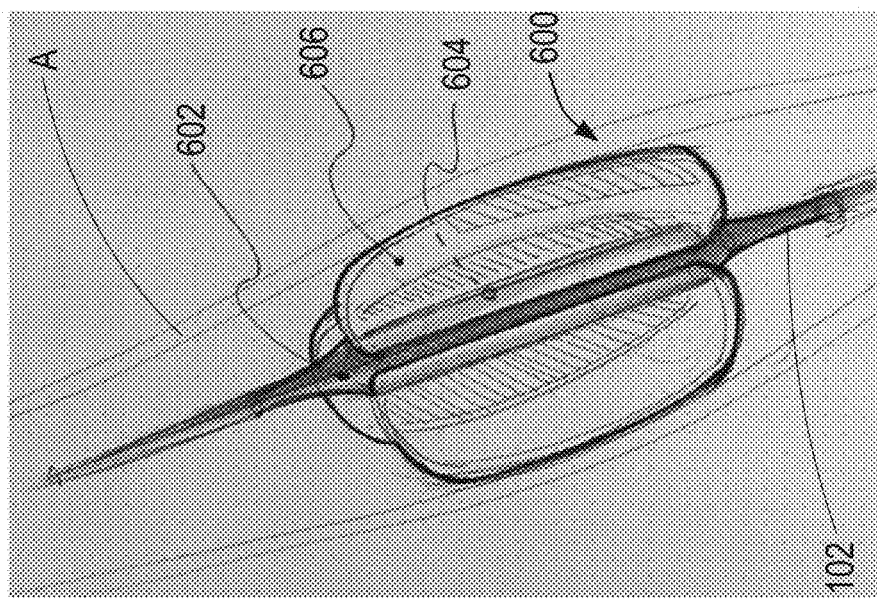
FIG. 6 illustrates a caged-balloon catheter constructed in accordance with the principles of the present disclosure.

Referring now to FIG. 6, a caged-balloon catheter constructed in accordance with the principles of the present disclosure is described. As shown in FIG. 6, expandable blood flow regulation device 104 of FIG. 1 may comprise caged-balloon catheter 600. Caged-balloon catheter 600 comprises non-compliant outer balloon 602 positioned at the distal end of catheter 102, and compliant inner balloon 606 enclosed within non-compliant outer balloon 602. Non-compliant outer balloon 602 includes one or more windows 604 sized to permit compliant inner balloon 606 to extrude therethrough when compliant inner balloon 606 is inflated. The number of windows correspond to the number of extrusions of compliant inner balloon 606 through non-compliant outer balloon 602. The shape of windows 604 controls the shape of compliant inner balloon 606 during partial inflation. Compliant balloon 606 is designed to be inflated to a carefully titrated balloon volume to regulate blood flow in the aorta. At full inflation, compliant inner balloon 606 may completely occlude the aorta. For example, an incompressible fluid may be introduced into compliant inner balloon 606 through a lumen of catheter 102 such that compliant inner balloon 606 may maintain the carefully titrated balloon volume. Compliant inner balloon 606 may be made of a suitable membrane that will prevent diffusion of the inflation fluid across the membrane and into the vasculature of the patient. The membrane may also be designed to inflate and deflate without undergoing morphological changes over time. As described above, caged-balloon catheter 600 may be placed within aorta A of the patient in series with additional caged-balloon catheter. The compliant inner balloons of each caged-balloon catheter may be individually inflated and deflated such that each caged-balloon catheter maintains its own carefully allocated carefully titrated balloon volume. The caged-balloon catheters may also be spaced apart along the distal end of catheter 102 such that the caged-balloon catheters are placed within different levels of the aorta. Any combination of the expandable blood flow regulation device embodiments described above may be used in series as will be understood by one skilled in the art.

Figure 7:
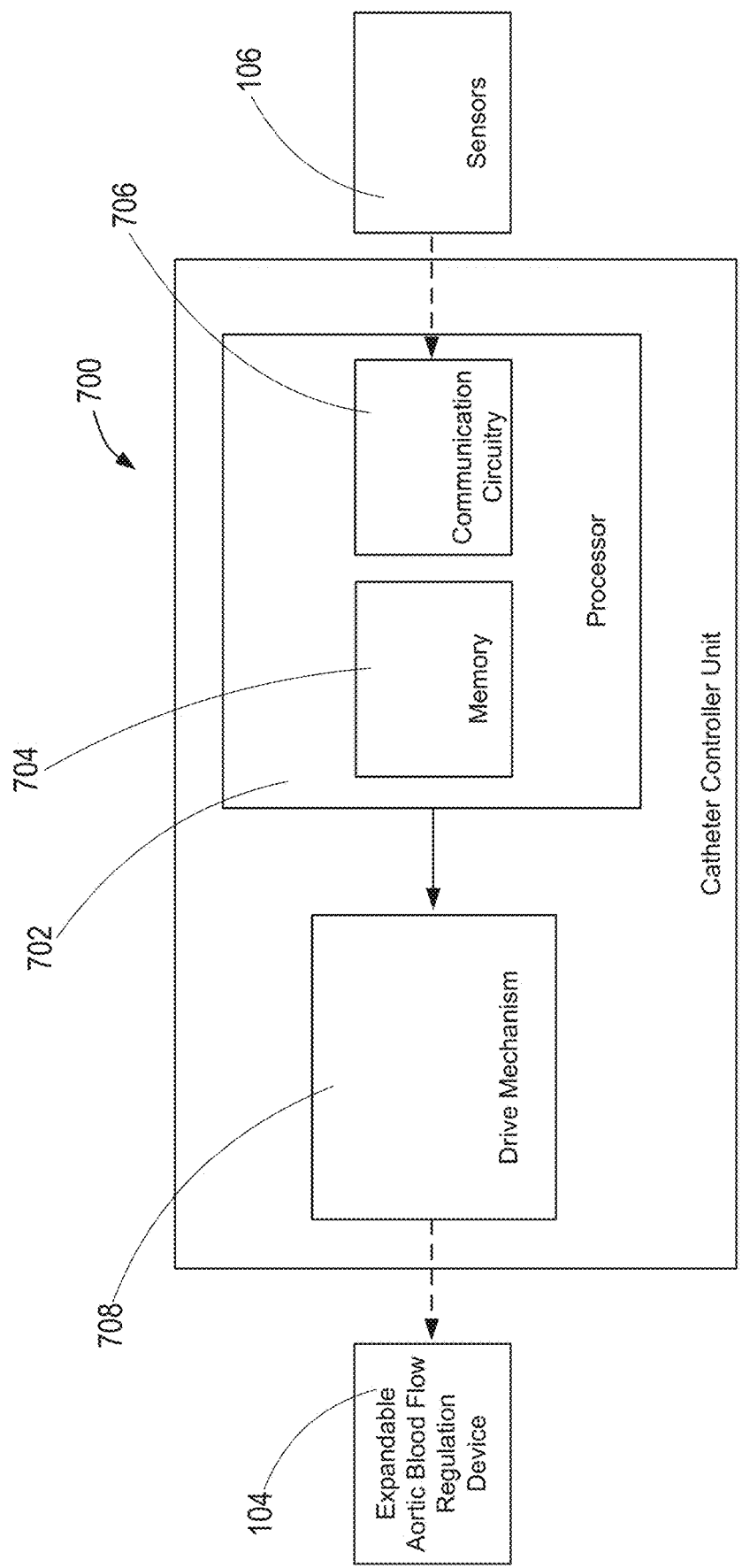
FIG. 7 is a schematic of an exemplary catheter controller unit constructed in accordance with the principles of the present disclosure.

Referring to FIG. 7, an exemplary catheter controller unit constructed in accordance with the principles of the present disclosure is described. As shown in FIG. 7, catheter controller unit 700 comprises processor 702 having memory 704 and communication circuitry 706, and drive mechanism 708. In FIG. 7, components of processor 702 are not depicted to scale on either a relative or absolute basis. Processor 702 may be operatively coupled to sensors 106 and drive mechanism 708, and drive mechanism 708 may be operatively coupled to expandable blood flow regulation device 104.

Processor 702 may receive data indicative of the measured physiological information from sensors 106 via communication circuitry 706. Memory 704, non-transitory computer readable media, may store a target physiological parameter and a corresponding range associated with blood flow through the aorta, and instructions that, when executed by processor 702, cause processor 702 to compare the measured physiological information with the target physiological range to determine whether the measured physiological information is within the predetermined target physiological range. As such, processor 702 may calculate an appropriate change in the amount of occlusion by expandable blood flow regulation device 104 necessary to bring the patient physiology within the target physiological range based on the current measured patient physiology.

Processor 702 comprises a series of sub-algorithms for controlling each aspect of appropriate balloon inflation, deflation, and rate of response to physiologic changes when a balloon-based catheter is used, e.g., balloon catheter 200, wire-over-balloon catheter 300, 400, or caged-balloon catheter 600, or when a wire-based catheter is used, e.g., wire-over-balloon catheter 300, 400 or intra-aortic sail catheter 500, the deployment, retraction and rate of change of the wire-based catheter. These individual algorithms may also calculate: initial calibration to identify the physical measurements of the vessel, determination of complete occlusion, identification of a working range of the catheter, e.g., the range of occlusion that results due to changes in patient physiology, set point optimization, weaning off from catheter-based physiologic support, and balloon volume tuning.

For balloon catheter 200, the balloon calibration sequence occurs upon initial insertion of the catheter or upon initiation of EPACC. The calibration sequence is also activated any time large changes in the hemodynamics are detected that are not induced by EPACC. Upon initiation of the balloon calibration sequence, drive mechanism 708 of catheter controller unit 700 will iteratively introduce small aliquots of gas or fluid, e.g., carbon dioxide, saline, or a mixture of contrast and saline, into the balloon. During sequential boluses, proximal physiology may be monitored until a change is observed, which denotes the low set point of the working range of balloon 204. Balloon 204 will continue to inflate until the distal blood pressure waveform is extinguished or until proximal physiologic changes are no longer observed, which denotes the upper working range of balloon catheter 200. Alternatively, the upper limit may be denoted by measuring the cessation of aortic flow. A mid-point of the working range may be set as an interval increase in balloon volume from the low set point and may be referenced for a rapid return to working range if needed during EPACC.

For wire-over-balloon catheters 300, 400 a similar calibration sequence may be followed. Initial low and high balloon set points are determined with iterative inflation of the balloon of the wire-over-balloon catheter while monitoring proximal physiology. After complete occlusion or when maximal inflation is achieved, the wires are immediately activated to allow for blood flow past the balloon. During wire activation, proximal and distal physiology may be monitored such that the degree of wire activation is noted when physiology is observed to no longer change. This set point denotes the low range of wire activation, with no wire activation denoted as the high range for wire activation.

For intra-aortic sail catheter 500, the calibration sequence is similar to the balloon catheter sequence except that the low and high points for set points are denoted based solely off of proximal physiologic changes, e.g., the point that proximal physiology begins to change and the point when no further change is observed.

After balloon calibration has occurred and initial balloon volume set points have been identified, processor 702 causes catheter controller unit 700 to adjust the shape and size of expandable blood flow regulation device 104 via drive mechanism 708 to augment proximal blood pressure responsive to patient physiology. As described above, processor 702 compares the measured physiological information received from sensors 106 with the target physiological range stored in memory 704 to determine whether the measured physiological information is within the predetermined target physiological range. For example, if proximal blood pressure is set as the physiologic marker, when processor 702 determines that proximal blood pressure drops below the target blood pressure range, catheter controller unit 700 expands expandable blood flow regulation device 104 via drive mechanism 708, e.g., inflate the balloon, decrease the wire tension in a wire-over-balloon catheter design, or expand the wire framework in an aortic sail design. Similarly, when processor 702 determines that proximal blood pressure exceeds the target blood pressure range, catheter controller unit 700 contracts expandable blood flow regulation device 104 via drive mechanism 708, e.g., deflate the balloon, increase the wire tension in a wire-over-balloon catheter design, or contract the tension of the wire framework in an aortic sail design. The amount of change in balloon volume or wire tension that occurs in response to blood pressure changes that are out of range is dependent upon how far the current measured blood pressure is from the target blood pressure. Therefore, if the blood pressure is only minimally out of the target range, a small change in size of expandable blood flow regulation device 104 is made. In contrast, when the blood pressure is significantly out of the target range, a larger change in size of expandable blood flow regulation device 104 is made. An example algorithm that may be used to provide EPACC includes:

$$uLBolus = (P_0 - P_s)^2 * V$$

where $P_0$ is current pressure, $P_s$ is set point pressure, and V is a constant described below. One skilled in the art will understand that alternative algorithms could be used to adjust balloon volumes based upon current and goal physiology.

The balloon tuning, wire tuning, or sail tuning algorithm allows for the magnitude of the change of size of expandable blood flow regulation device 104 in response to the difference between the measured physiological information and the target physiological parameter to be dynamic, controlled by the constant V. Initially V may be set to a default, but V may change dynamically dependent upon the magnitude of physiologic changes that occur beyond the initial target set points. For example, if blood pressure is set as the physiologic marker and the initial blood pressure recorded by sensors 106 was below the set point pressure, but the resulting blood pressure recorded by sensors 106 after the change in expansion amount of expandable blood flow regulation device 104 by drive mechanism 708 is above the set point pressure, V would then be modified in order to correct for overshooting the goal set point. If the measured blood pressure is determined to be within the target blood pressure and as a result, the amount of expansion of expandable blood flow regulation device 104 drops below the low set point, expandable blood flow regulation device 104 will then wean off to its baseline zero set point. This may occur by either deflating the balloon, further indenting the balloon, or by retracting the intra-aortic sail.

As described above, processor 702 may automatically expand and contract expandable blood flow regulation device 104 via drive mechanism 708 in accordance with the principles of the present disclosure. For example, when expandable blood flow regulation device 104 comprises balloon catheter 200 or caged-balloon catheter 600, drive mechanism 708 may be a syringe pump designed to inject or remove fluid from the balloon to inflate or deflate the balloon via the exit ports in fluid communication with the lumen of catheter 102. The syringe pump may make small titrated changes in balloon volume in response to patient physiology via automation.

As described above, the balloon catheters may be placed in series within the aorta and may be individually inflated and deflated such that each balloon catheter maintains its own allocated carefully titrated balloon volume. As such, the syringe pump of drive mechanism 708 may be operatively coupled to the balloons via multiple lumens extending through catheter 102. For example, one lumen may permit the syringe pump to inject or remove fluid from the balloon placed in zone 1 of the aorta, while another lumen may permit syringe pump to inject or remove fluid from the balloon placed in zone 3 of the aorta. As such, blood pressure may be regulated in different levels of the aorta.

When expandable blood flow regulation device 104 comprises wire-over-balloon catheter 300, 400, drive mechanism 708 may comprise a syringe pump designed to insert or remove fluid from the balloon to inflate or deflate the balloon via the exit ports in fluid communication with the lumen of catheter 102 as described above, and a controller arm designed to manipulate the wires that overlie the balloon to tighten or loosen the wire against the balloon, allowing for careful titrated changes in balloon indentation in response to patient physiology via automation. For example, the controller arm of drive mechanism 708 may include a stepper motor that may shorten or lengthen the wires relative to a fixed point at the proximal end of catheter 102, or a motorized arm that may tighten or loosen the wires to change the tension of the wires relative to a fixed point at the proximal end of catheter 102. One skilled in the art will realize that alternative methods for changing the length of the wire over the balloon could be used.

As described above, the wire-over-balloon catheters may be placed in series within the aorta and may be individually indented such that each wire-over-balloon catheter maintains its own allocated carefully allocated degree of indentation. As such, the syringe pump of drive mechanism 708 may be operatively coupled to the balloons via multiple lumens extending through catheter 102. For example, one lumen may permit the syringe pump to inject or remove fluid from the balloon placed in zone 1 of the aorta, while another lumen may permit syringe pump to inject or remove fluid from the balloon placed in zone 3 of the aorta. Similarly, the controller arm of drive mechanism 708 may be operatively coupled to the wires of each wire-over-balloon catheter via multiple lumens extending through catheter 102 such that one lumen may permit the controller arm to tighten or loosen the wires of the wire-over-balloon catheter placed in zone 1 of the aorta, while another lumen may permit the controller arm to tighten or loosen the wires of the wire-over-balloon catheter placed in zone 3 of the aorta. As such, blood pressure may be regulated in different levels of the aorta.

When expandable blood flow regulation device 104 comprises intra-aortic sail catheter 500, drive mechanism 708 may comprise a controller arm designed to manipulate wire framework 502 in response to patient physiology via automation. As described above, the controller arm of drive mechanism 708 may include a stepper motor that may shorten or lengthen the wires of wire framework 502 relative to a fixed point at the proximal end of catheter 102, or a motorized arm that may tighten or loosen the wires to change the tension of the wires of wire framework 502 relative to a fixed point at the proximal end of catheter 102.

As described above, the intra-aortic sail catheters may be placed in series within the aorta and may be individually expanded such that each intra-aortic sail catheter maintains its own carefully allocated degree of expansion. As such, the controller arm of drive mechanism 708 may be operatively coupled to the wire framework of each intra-aortic sail catheter via multiple lumens extending through catheter 102. For example, one lumen may permit the controller arm to tighten or loosen the wire framework of the intra-aortic sail catheter placed in zone 1 of the aorta, while another lumen may permit the controller arm to tighten or loosen the wire framework of the intra-aortic sail catheter placed in zone 3 of the aorta. As such, blood pressure may be regulated in different levels of the aorta. As described above, any combination of the aforementioned expandable blood flow regulation device embodiments may be used in series as will be understood by one skilled in the art. Accordingly, drive mechanism 708 may comprise any combination of the syringe pump and controller arms to provide unique expansion and control of the individual expandable blood flow regulation devices.

After each change in balloon volume or wire tension by drive mechanism 708 of catheter controller unit 700, processor 702 may wait for a predetermined period of time for the resulting physiologic response to be monitored before further adjusting the balloon volume or wire tension.

In one embodiment, drive mechanism 708 may provide for manual inflation of the balloon or manual tightening of the wires, e.g., when automation is either unavailable or not feasible. For example, a manual drive mechanism may include a syringe pump that may inject fluid using the normal action of a syringe, but may also inject or remove fluid via screw actuation once threads on the plunger and within the barrel of the syringe have been activated. Injection via normal syringe plunging, but fluid removal only via screw actuation allows for rapid inflation of the balloon, but carefully titrated removal of fluid based upon the pitch of the thread on the plunger.

In one embodiment, processor 702 may identify via sensors 106 when a patient requires more intravenous fluids, and communicate with and instruct an external pump to provide IV fluids to the patient. In another embodiment, processor 702 may identify via sensors 106 when increases or decreases in vasopressor medications are needed, and communicate with and instruct an external pump to adjust the amount of vasopressors administered to the patient.

Figure 8:
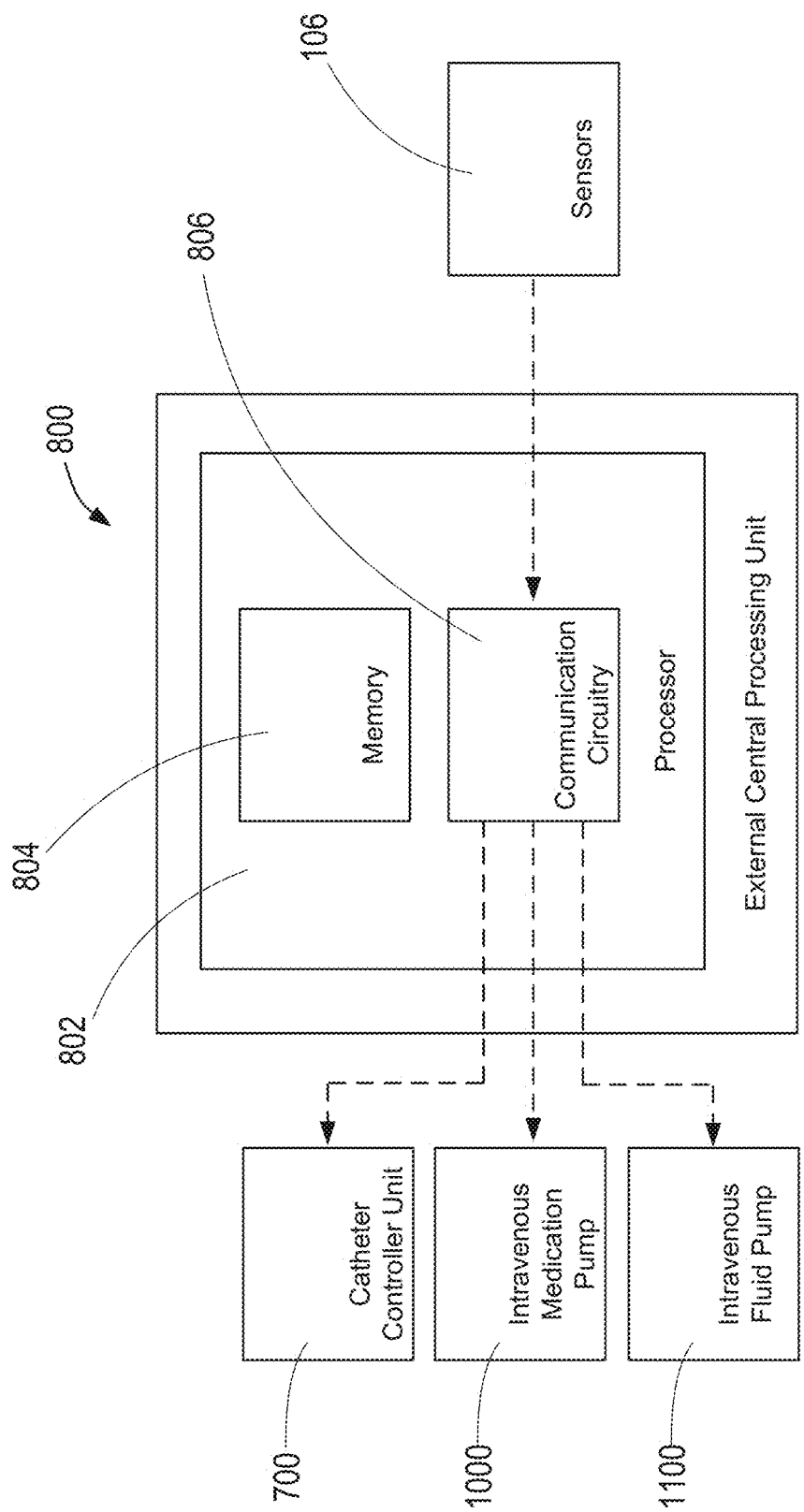
FIG. 8 is a schematic of an exemplary external central processing unit constructed in accordance with the principles of the present disclosure.

Referring to FIG. 8, an exemplary external central processing unit constructed in accordance with the principles of the present disclosure is described. As shown in FIG. 8, external central processing unit 800 comprises processor 802 having memory 804 and communication circuitry 806. In FIG. 8, components of processor 802 are not depicted to scale on either a relative or absolute basis. Processor 802 may be constructed similarly to processor 702 of catheter controller unit 700 of FIG. 7, such that processor 802 may be operatively coupled to sensors 106, receive data indicative of the measured physiological information from sensors 106, and compare the measured physiological information with a target physiological range stored in memory 804. When system 100 comprises external central processing unit 800, processor 802 of external central processing unit 800 determines whether the measured physiological information is within the target physiological range, calculates information indicative of the appropriate change in the amount of occlusion by expandable blood flow regulation device 104 required to bring the patient's physiology within the target physiological range if the measured physiological information falls outside the target physiological range, and transmits the information to catheter controller unit 700 via communication circuitry 806. For example, communication circuitry 806 of external central processing unit 800 may transmit the information to communication circuitry 706 of catheter controller unit 700 via at least one of WiFi, Bluetooth, Wixel-based communication, or cellular communication, or a wired connection.

In one embodiment, system 100 may comprise intravenous medication pump 1000. Intravenous medication pump 1000 may deliver vasoactive medications to the patient through a peripherally placed or centrally placed IV. Processor 802 of external central processing unit 800 may determine whether the measured physiological information is within a target physiological range associated with various physiologic parameters, e.g., blood pressure, heart rate, indices of tissue perfusion including measured blood flow, calculate information indicative of the appropriate change in the amount of vasoactive medications required to bring the patient's physiology within the target physiological range if the measured physiological information falls outside the target physiological range, and transmit the information to intravenous medication pump 1000 via communication circuitry 806, e.g., via at least one of WiFi, Bluetooth, Wixel-based communication, or cellular communication, or a wired connection. Intravenous medication pump 1000 may deliver vasoactive medications to the patient to modulate, e.g., raise or lower, patient physiology, e.g., heart rate, systemic blood pressure or pressure within discreet regions of the body, blood flow in the aorta, or other markers including mathematical relationships derived therefrom, based on the information received from external central processing unit 800. In one embodiment, intravenous medication pump 1000 may include its own processor operatively coupled to sensors 106 such that intravenous medication pump 1000 receives data indicative of the measured physiological information from sensors 106 directly, compares the measured physiological information with the target physiological range, and delivers vasoactive medications to the patient based on the comparison.

In one embodiment, system 100 may comprise intravenous fluid pump 1100. Intravenous fluid pump 1100 may deliver fluids and/or blood products to the patient through a peripherally placed or centrally placed IV. Processor 802 of external central processing unit 800 may determine whether the measured physiological information is within a target physiological range associated with various physiologic parameters, e.g., blood pressure, heart rate, indices of tissue perfusion including measured blood flow, calculate information indicative of the appropriate change in the amount of vasoactive medications required to bring the patient's physiology within the target physiological range if the measured physiological information falls outside the target physiological range, and transmit the information to intravenous fluid pump 1100 via communication circuitry 806, e.g., via at least one of WiFi, Bluetooth, Wixel-based communication, or cellular communication, or a wired connection. Intravenous fluid pump 1100 may deliver fluids and/or blood products to the patient to modulate, e.g., raise or lower, patient physiology, e.g., heart rate, systemic blood pressure or pressure within discreet regions of the body, blood flow in the aorta, or other markers including mathematical relationships derived therefrom, based on the information received from external central processing unit 800. In one embodiment, intravenous fluid pump 1100 may include its own processor operatively coupled to sensors 106 such that intravenous fluid pump 1100 receives data indicative of the measured physiological information from sensors 106 directly, compares the measured physiological information with the target physiological range, and delivers fluids and/or blood products to the patient based on the comparison.

Figure 9:
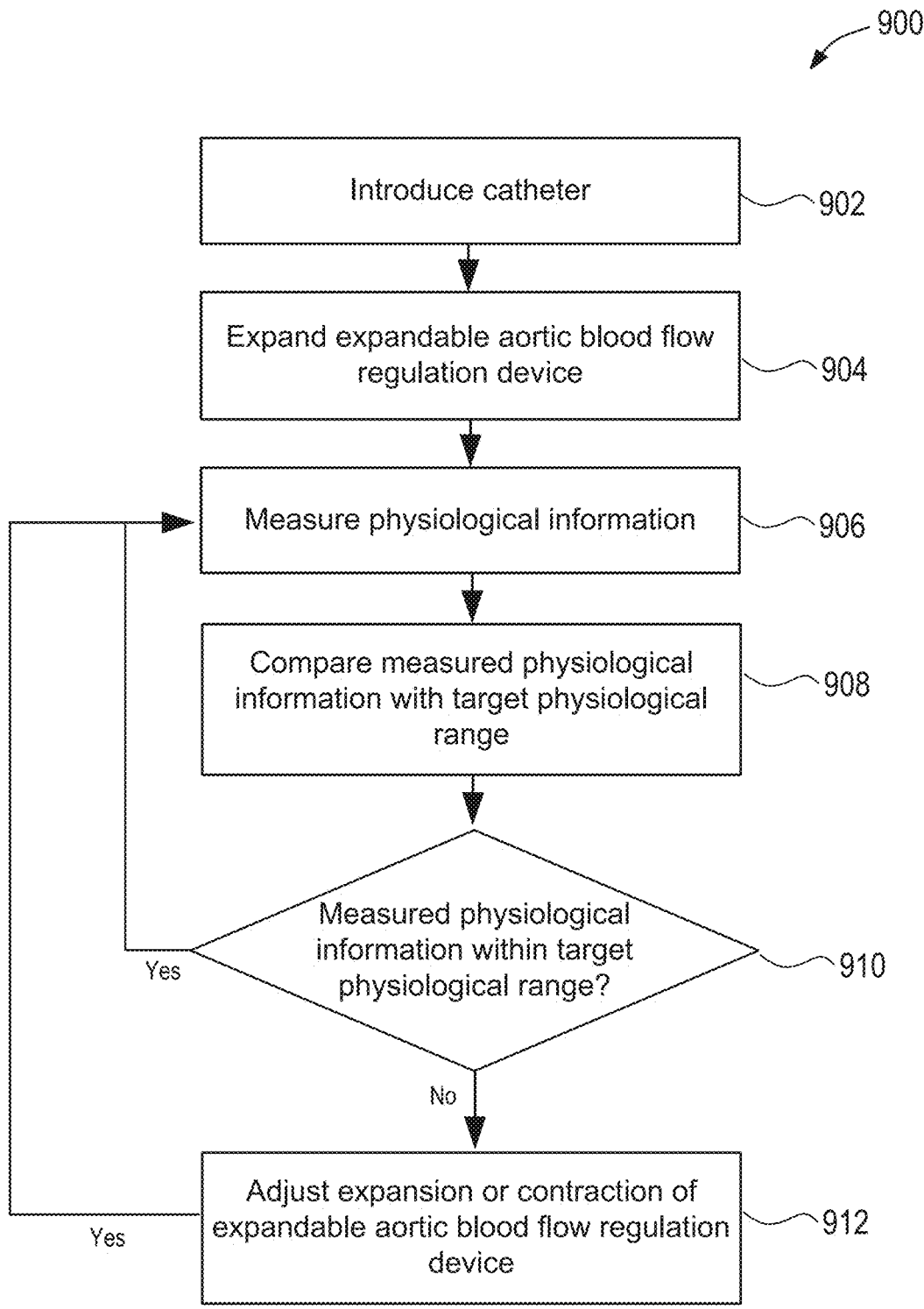
FIG. 9 is a flow chart illustrating an exemplary method for automatically, dynamically regulating the degree of aortic blood flow regulation for endovascular perfusion augmentation in accordance with the principles of the present disclosure.

Referring to FIG. 9, an exemplary method for automatically, dynamically regulating the degree of aortic blood flow regulation for endovascular perfusion augmentation in accordance with the principles of the present disclosure is described. Method 900 may be used to perform EPACC on a patient, for example, in shock from sepsis or trauma. At step 902, distal end 103 of catheter 102 is introduced into the patient via the femoral artery or the radial artery such that expandable blood flow regulation device 104 disposed at distal end 103 is placed within the aorta. As described above, expandable blood flow regulation device 104 may comprise balloon catheter 200, wire-over-balloon catheter 300, 400, intra-aortic sail catheter 500, or caged-balloon catheter 600. In one embodiment, catheter 102 may comprise multiple expandable blood flow regulation devices such that one expandable blood flow regulation device is placed within a zone, e.g., zone 1, of the aorta and another expandable blood flow regulation device is placed in a different zone, e.g., zone 3, of the aorta.

At step 904, expandable blood flow regulation device 104 may be expanded to regulate blood flow through the aorta. For example, drive mechanism 708 of catheter controller unit 700 may cause balloon 204 of balloon catheter 200 to be inflated such that it regulates blood flow in the aorta; balloon 304, 404 of wire-over-balloon catheter 300, 400 to be inflated such that it completely occludes the aorta, immediately followed by the tightening of wires 306, 406 to indent balloon 304, 404 such that it only partially occludes the aorta; wire framework 502 to be expanded such that thin membrane 504 only partially occludes the aorta; and/or compliant inner balloon 606 to be inflated such that it extrudes through windows 604 of non-compliant outer balloon 602 to only partially occludes the aorta.

At step 906, sensors 106 may measure physiological information indicative of blood flow through the aorta. For example, as described above, sensors 106 may measure information indicative of blood pressure, heart rate, central venous pressure, peripheral vascular resistance, respiratory rate, pulmonary pressures, and intracranial pressure. Sensors 106 may comprise one or more sensors positioned proximal and/or distal to each expandable blood flow regulation device utilized to effectively monitor patient physiology.

At step 908, processor 702 of catheter controller unit 700, or when external central processing unit 800 is utilized, processor 802, may compare the measured physiological information with a target physiological range, and at step 910, determine whether the measured physiological information falls within the target physiological range. If it is determined at step 910 that the measured physiological information falls within the target physiological range, method 300 may maintain the current state of expansion of expandable blood flow regulation device 104 and return to step 906 to continue measuring physiological information of the patient. If it is determined at step 910 that the measured physiological information falls outside the target physiological range, e.g., exceeds or falls below the target physiological range, catheter controller until 700 may determine the amount of change in expansion of expandable blood flow regulation device 104 necessary to bring patient physiology within the target physiological range, and at step 912, cause drive mechanism 708 to adjust the expansion or contraction of the expandable blood flow regulation device, e.g., inflate or deflate balloon or tighten or loosen wires, to adjust the amount of blood flow through the aorta. When external central processing unit 800 is utilized, processor 802 transmits informative indicative of the amount of change in expansion of expandable blood flow regulation device 104 necessary to bring patient physiology within the target physiological range, determined at step 910, to catheter controller unit 700 via communication circuitry 806 and 706 before proceeding to step 912.

Study Comparing EPACC and Standard Critical Care

Figure 10:
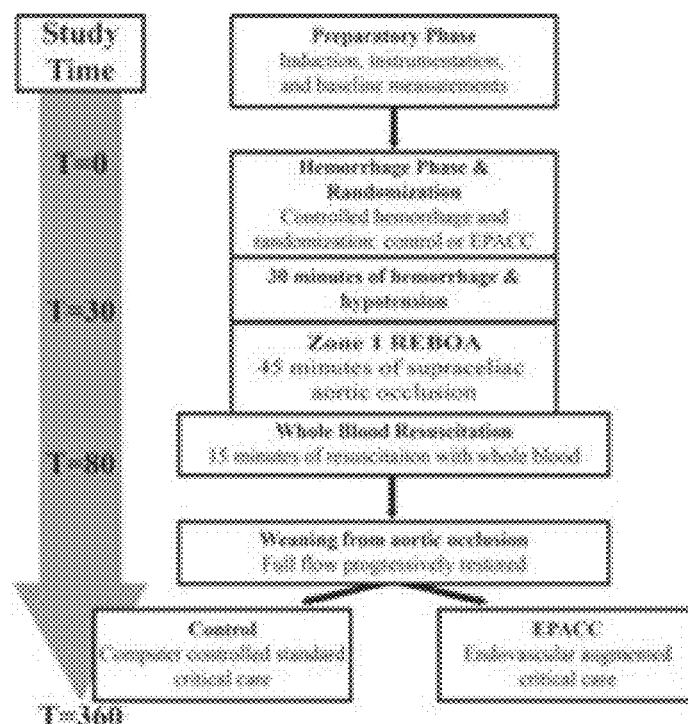
FIG. 10 is a flow chart illustrating a study comparing EPACC and Standard Critical Care.

A study comparing EPACC and Standard Critical Care (STD) was approved by The Institutional Animal Care and Use Committee at David Grant Medical Center, Travis Air Force Base. The study flow is outlined in FIG. 10. For example, first, healthy adult, castrate male and non-pregnant female Yorkshire-cross swine (*Sus scrofa*) weighing between 60 and 95 kg were acclimated for a minimum of 10 days prior to experimentation. A hemorrhagic shock ischemia-reperfusion injury was created by performing a splenectomy followed by a 30-minute controlled hemorrhage of 25% of total blood volume. The ensuing hypotension was treated with 45 minutes of descending thoracic aortic occlusion to improve proximal hemodynamics and induce distal body ischemia. Following the 45-minute occlusive phase, all animals were resuscitated with their shed blood before randomization into one of two critical care groups—STD or EPACC. STD was provided via an automated critical care platform that delivered crystalloid fluid boluses and titration of vasopressors based on a predefined critical care algorithm described in further detail below. Animals randomized to EPACC were provided with automated partial aortic occlusion of the descending thoracic aorta to maintain blood pressure within target range (proximal mean arterial pressure 60-70 mmHg), with a minimum aortic flow threshold of 80% of baseline aortic flow (BAF) (weight-based estimation). As will be understood by one having ordinary skill in the art, other minimum aortic flow thresholds may be used. For example, lower thresholds such as 60% BAF or higher thresholds such as 120%, e.g., if the patient is in a hyper dynamic (low blood pressure but very high cardiac output). Once flow reached this threshold due to progressive balloon inflation, no further balloon support was provided. To increase blood pressure towards the goal range in this scenario, the same automated IV fluid and vasopressor administration algorithm as the STD group was applied. After a total study duration of 6 hours, the animals were sacrificed and underwent necropsy with histologic analysis of organs.

Specifically, animals were fasted for 12 hours prior to experimentation. Animals were pre-medicated with 6.6 mg/kg intramuscular tiletamine/zolazepam (TELAZOL, Fort Dodge Animal Health, Fort Dodge, Iowa). Following isoflurane induction and endotracheal intubation, general anesthesia was maintained with 2% isoflurane in 100% oxygen. All animals received a 1 liter bolus of Plasma-Lyte (Baxter, Deerfield, Ill.) to ensure fluid optimization at the onset of the experiment. To offset the vasodilatory effects of general anesthesia, an intravenous infusion of norepinephrine (0.01 mg/kg/min) was instituted upon venous access, and titrated prior to experimentation to achieve a target mean arterial pressure between 65 and 75 mm Hg. Animals were mechanically ventilated to maintain end-tidal $CO_2$ at 40±5 mm Hg. During initial surgical preparation, plasmalyte maintenance IV fluid was administered at a rate of 10 mL/kg/h until the abdomen was closed. After abdominal closure maintenance fluids were continued at 5 mL/kg/h for the remainder of the study. Intravenous heparin was administered to achieve an activated clotting time (ACT) of 100 seconds. An underbody warmer was used to maintain core body temperature between 35 and 37° C. and a hot-air body warmer was instituted if core body temperature dropped below 35° C.

Following a generous laparotomy and placement of a cystotomy tube, a splenectomy was performed to minimize hemodynamic variation from autotransfusion. The supraceliac aorta was exposed by dividing the left diaphragm and incising the left inferior pulmonary ligament. The aorta was dissected circumferentially for a length of 5-10 cm and two adjacent intercostal arteries were ligated. A perivascular flow probe (Transonic, Ithaca, N.Y.) was placed proximally to the two ligated intercostal arteries. Additional flow probes were placed on the right carotid artery and the left renal artery. Following a right renal biopsy, the abdomen was closed with cable ties. Following surgical cutdown, a 7 Fr arterial sheath (Teleflex, Morrisville, N.C.) was placed in the right common femoral artery, a 12 F arterial sheath (Teleflex, Morrisville, N.C.) was placed in the left common femoral artery. A dual lumen 10 Fr venous resuscitation line (Cook Medical, Bloomington, Ind.) was placed in the left femoral vein for blood transfusion and resuscitation fluids. Bilateral external jugular veins were surgically exposed and cannulated with a 7 Fr triple lumen catheter (Cook Medical, Bloomington, Ind.) and a 7 Fr arterial sheath (Teleflex, Morrisville, N.C.) to allow for maintenance fluid and vasoactive medication administration. A 9 Fr arterial sheath (Teleflex, Morrisville, N.C.) was placed in the left axillary artery after surgical exposure for proximal blood pressure measurements. The right brachial artery was exposed and cannulated with a 7 Fr sheath (Teleflex, Morrisville, N.C.) to facilitate initial hemorrhage. A CODA-LP catheter (Cook Medical, Bloomington, Ind.) was introduced through the left femoral 12 Fr arterial sheath and positioned just distal to the aortic flow probe.

Physiologic measurements of proximal and distal blood pressure, aortic blood flow, renal blood flow, carotid blood flow, heart rate, central venous pressure, and core temperature were collected in real time with a Biopac MP150 (Biopac Corporation, Goleta, Calif.) multichannel data acquisition system. A complete blood count and basic metabolic panel were collected at the start of the experiment prior to euthanasia. Arterial blood gases, urine, and serum were collected routinely throughout the experiment and urine and serum were frozen at −80° C. for later analysis. Following euthanasia, a necropsy was performed with notation of any gross anatomic abnormalities. Heart, lungs, brain, kidney, aorta, small and large bowel, and distal muscular tissue were sampled and fixed for pathologic and histologic analysis by a veterinarian blinded to the treatment groups. Histologic scoring was defined as: 0 (no evidence), 1 (minimal), 2 (minor), 3 (moderate), and 4 (severe).

The automated care platform consisted of four devices capable of wireless communication. A microprocessor within a central processing unit (CPU) received physiologic data from the BioPac data acquisition system, and the CPU wirelessly transmitted instructions based on predefined algorithms to three peripheral devices; an automated syringe pump controlling an endovascular catheter, a syringe pump titrating the administration of norepinephrine, and a peristaltic pump providing IV crystalloid boluses.

Following blood resuscitation, the animals were randomized to either the EPACC arm or the STD arm of the experiment. Animals in the EPACC group received automated endovascular support using the wireless automated syringe pump running custom closed loop adaptive feedback algorithms to control the balloon volume of the CODA LP in Zone I of the aorta, as outlined below.

If pMAP <60 mmHg and CVP <7 mmHg and Aortic flow >80% of weight based normal→increase balloon support
If pMAP <60 mmHg and CVP <7 mmHg and Aortic flow <80% of weight based normal→decrease balloon support
If pMAP <60 mmHg and CVP <7 mmHg and Aortic flow <80% of weight based normal→fluid bolus and increase NE by 0.02 mcg/kg/min
If pMAP <60 mmHg and CVP 7-9 mmHg and Aortic flow <80% of weight based normal→fluid bolus and increase NE by 0.01 mcg/kg/min
If pMAP <60 mmHg and CVP >9 mmHg and Aortic flow <80% of weight based normal→increase NE by 0.01 mcg/kg/min
If pMAP <60 mmHg and CVP >9 mmHg and Aortic flow <80% of weight based normal→and NE=0.2 mcg/kg/min→fluid bolus
If pMAP 60-70 mmHg do nothing
If pMAP >70 mmHg→decrease NE by 0.01 mcg/kg/min For example, when the mean arterial proximal (pMAP) blood pressure fell below 60 mmHg and aortic flow exceeded 80% of BAF, endovascular support would be provided via partial balloon inflation. If aortic flow dropped below 80% of BAF, the degree of aortic occlusion was decreased by reducing balloon volume until aortic flow returned to the target threshold. As described above, higher or lower minimum aortic flow thresholds of BAF may be used depending on the patient's condition. If persistent hypotension developed, crystalloid boluses and norepinephrine would be provided through the standard critical care algorithm, based on continuous CVP and mean arterial blood pressure readings proximal to the CODA LP balloon.

Animals in the STD arm of the study were administered crystalloid boluses and had titration of vasopressor based on a standard protocol, as outlined below.
If pMAP <60 mmHg and CVP <7 mmHg→fluid bolus and increase NE by 0.02 mcg/kg/min
If pMAP <60 mmHg and CVP 7-9 mmHg→fluid bolus and increase NE by 0.01 mcg/kg/min
If pMAP <60 mmHg and CVP >9 mmhg→increase NE by 0.01 mcg/kg/min
If pMAP <60 mmHg and CVP >9 mmHg and NE=0.2 mcg/kg/min→fluid bolus
If pMAP 60-70 mmHg do nothing
If pMAP >70 mmHg→decrease NE by 0.01 mcg/kg/min The target MAP range was defined as 60-70 mmHg for the critical care phase, a priori. Animals with a blood pressure greater than 70 mmHg were weaned from vasopressor medications preferentially until initial vasopressor medication doses were met prior to having balloon support weaned. Once vasopressor medications reached baseline rates, balloon support was weaned until full restoration of flow.

Data analysis was performed with STATA version 14.0 (Stata Corporation, Bryan, Tex.). Continuous variables are presented as means and standard errors of the means if normally distributed and as medians with interquartile ranges if not distributed normally. T-tests were used to compare normally distributed continuous data and Wilcoxson rank sum tests were used for data that was not normally distributed. Dichotomous and categorical variables were analyzed by Chi-squared test and presented as percentages. Statistical significance was set at $p<0.05$.

As shown in Table 1 below, there were no significant differences in baseline characteristics or initial laboratory parameters between the STD and EPACC groups.

TABLE 1

Baseline Characteristics

|  | STD (n = 6) | EPACC (n = 6) | P |
|---|---|---|---|
| Sex |  |  | 1.0 |
| Male | 4 (66.7) | 4 (66.7) |  |
| Female | 2 (33.3) | 2 (33.3) |  |
| Weight (kg) | 77.5 (8.0) | 77.0 (3.5) | 0.89 |
| pH | 7.4 (0.0) | 7.4 (0.0) | 0.94 |
| PiO$_2$:FiO$_2$ Ratio | 373 (96) | 409 (83) | 0.50 |
| Hemoglobin | 10.3 (0.8) | 10.0 (0.8) | 0.49 |
| White Blood Cells | 15.2 (3.0) | 12.9 (1.7) | 0.13 |
| Platelets | 275 (45) | 292 (105) | 0.73 |
| Potassium (mEq) | 3.7 (0.2) | 3.6 (0.2) | 0.51 |
| Lactate (mg/dL) | 2.4 (0.5) | 3.0 (0.7) | 0.14 |
| Creatinine | 1.3 (0.13) | 1.4 (0.2) | 0.49 |
| Glucose | 93 (8) | 87 (7) | 0.20 |
| Proximal MAP (mmHg) | 66 (7) | 67 (8) | 0.90 |
| Aortic Flow (ml/kg) | 38.3 (4.9) | 36.7 (9.3) | 0.72 |

Following the hemorrhage phase, both groups of animals had similar decreases in blood pressure.

As shown in Table 2 below, during aortic occlusion, there were no significant differences in maximum proximal MAP or average proximal MAP (pMAP-proximal mean arterial pressure; dMAP-distal mean arterial pressure).

TABLE 2

Hemodynamics Between Treatment Groups

|  | STD (n = 6) | EPACC (n = 6) | p-value |
|---|---|---|---|
| Min. pMAP Hemorrhage (mmHg) | 33 (29-36) | 31 (26-37) | 0.63 |
| Ave. pMAP Intervention (mmHg) | 129 (105-151) | 113 (101-123) | 0.20 |
| Max. pMAP Intervention (mmHg) | 161 (141-182) | 152 (142-160) | 0.15 |
| Average pMAP Critical Care (mmHg) | 60 (57-63) | 65 (64-66) | <0.01 |
| Time at Goal pMAP Critical Care (%) | 51.0 (29.5-72.6) | 95.3 (93.2-97.4) | <0.01 |
| Ave. dMAP Critical Care (mmHg) | 55 (51-59) | 42 (38-46) | <0.01 |
| Ave. Aortic Flow Critical Care (ml/min) | 3960 (3176-4743) | 2680 (2376-2984) | 0.01 |
| Ave. Aortic Flow Critical Care (mL/kg/min) | 51 (41-61) | 35 (32-38) | <0.01 |

Figure 11:
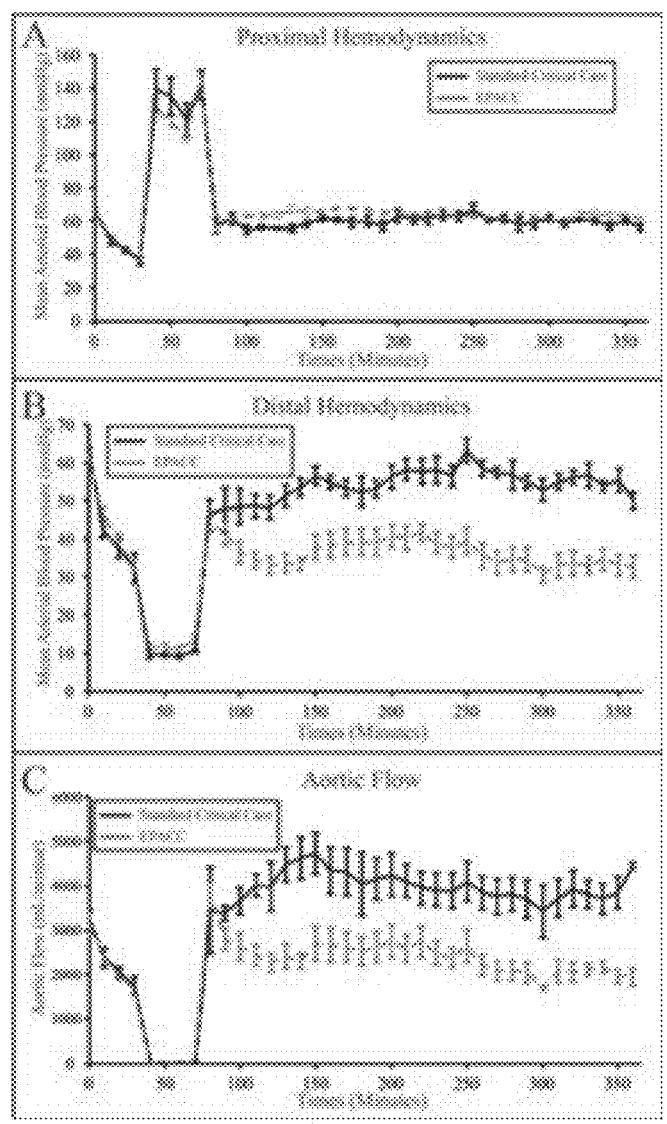
FIG. 11 illustrates charts depicting hemodynamic data derived from the study comparing EPACC and Standard Critical Care.
Figure 12:
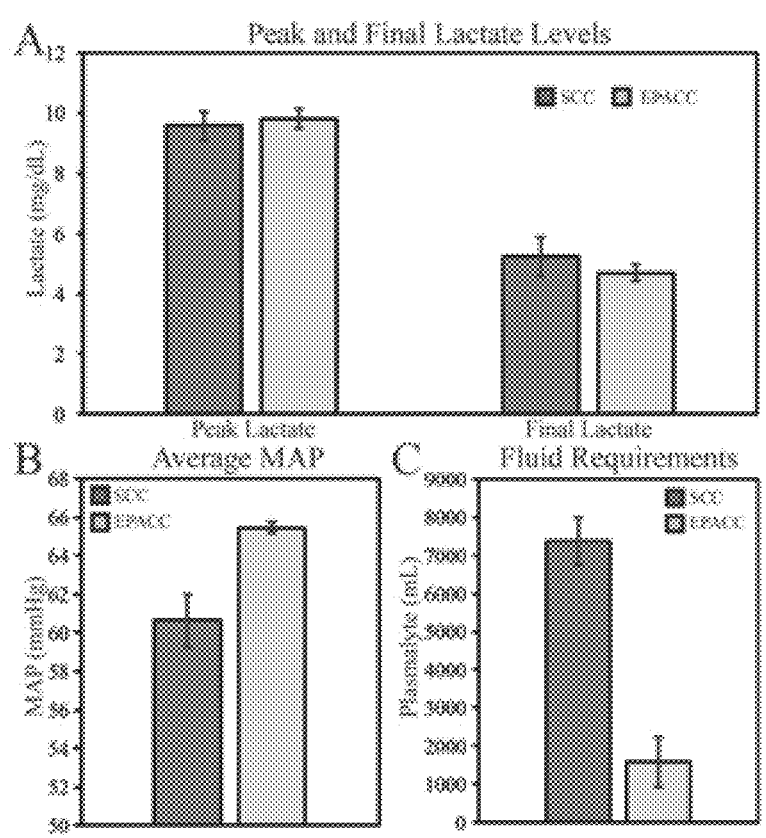
FIG. 12 illustrates charts depicting primary outcomes of interest derived from the study comparing EPACC and Standard Critical Care.

During the critical care phase, animals in the EPACC group had a higher average MAP (EPACC 65 mmHg, 95CI 64-66; STD 60 mmHg, 95CI 57-63; p<0.01), a lower distal MAP (EPACC 42 mmHg, 95CI 38-46; STD 55 mmHg, 95CI 51-59; p<0.01) and a lower aortic flow (EPACC 35 ml/kg/min, 95CI 32-38; STD 51 ml/kg/min, 95CI 41-46; p=0.01), as shown in FIGS. 11 and 12. As shown in FIG. 11, EPACC animals remained within goal proximal MAP during critical care for a greater period of time when compared to the STD animals (EPACC 95.3%, 95CI 93.2-97.4; STD 51.0%, 95CI 29.5-72.6; p<0.01).

Referring to FIG. 12, and as shown in Table 3 below, immediately after balloon deflation there were no significant differences in the maximum lactate (STD 9.6 mg/dL, 95CI 8.5-10.7; EPACC 9.8 mg/dL, 95CI 9.1-10.6; p=0.87).

TABLE 3

Interventions and laboratory values between groups

|  | STD (n = 6) | EPACC (n = 6) | p-value |
|---|---|---|---|
| Maximum Lactate (mg/dL) | 9.6 (8.5-10.7) | 9.8 (9.1-10.6) | 0.87 |
| Total Resuscitation Boluses (ml) | 7400 (6148-8642) | 1583 (12-3154) | <0.01 |
| Total Resuscitation Boluses (ml/kg) | 96 (76-117) | 21 (0-42) | <0.01 |
| Final $PiO_2$:$FiO_2$ Ratio | 259 (103-414) | 320 (234-405) | 0.63 |
| Final Creatinine (mg/dL) | 1.7 (1.4-2.0) | 2.3 (2.1-2.5) | <0.01 |
| Final Lactate (mg/dL) | 5.2 (3.7-6.8)) | 4.7 (4.1-5.3) | 0.52 |
| Hypoglycemic Episode During Critical Care (%) | 4 (66.7%) | 1 (16.7%) | 0.08 |

During the critical care portion of the study, the EPACC animals required less intravenous crystalloids when compared to the STD group (EPACC 21 ml/kg mg/dL, 95CI 0-42; STD 96 ml/kg, 95CI 76-117; p<0.01), required a lower dose of norepinephrine (EPACC 5 mcg/kg/min, 95CI 0-16; STD 51 mcg/kg/min, 95CI 37-64; p<0.01), and the EPACC group had a lower incidence of hypoglycemic episodes during the critical care phase of the study (EPACC 1 of 6 animals, 16.7%; STD 4 of 6 animals, 66.7%, p=0.08), as shown in FIG. 13.

Figure 13:
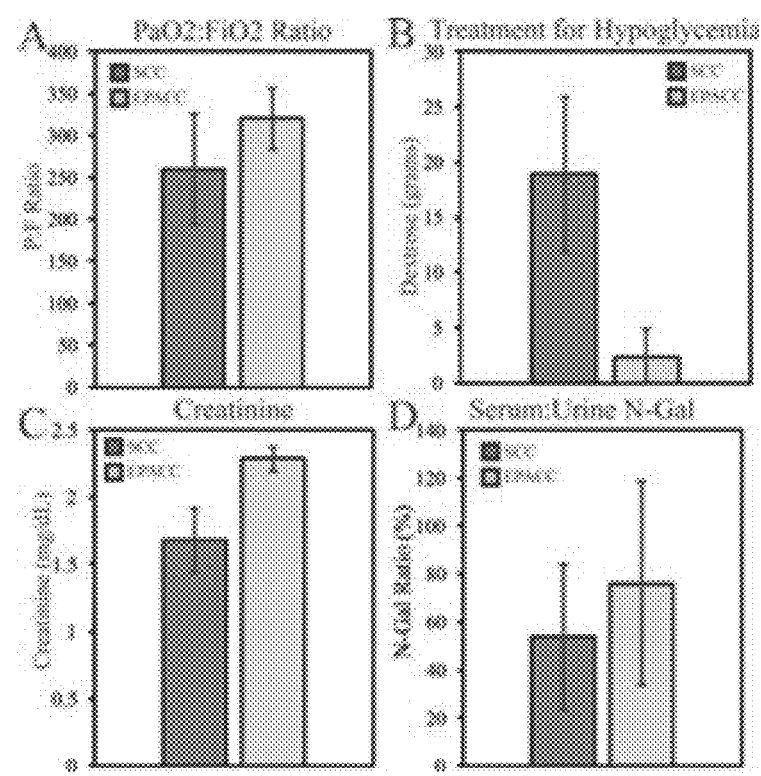
FIG. 13 illustrates charts depicting secondary outcomes of interest derived from the study comparing EPACC and Standard Critical Care.

As shown in FIG. 13, by the end of the study, there were no differences in final lactate or final P:F ratio, but animals in the EPACC group had a higher creatinine (EPACC 2.3 mg/dL, 95CI 2.1-2.5; STD 1.7 mg/dl, 95CI 1.4-2.0; p<0.01). In addition, there were no differences in the ratio of urine N-Gal to serum N-Gal between groups (EPACC 76.0%, 95CI 0-185.1; STD 53.7%, 95CI 0-132). Animals in the EPACC group had more edema within the kidneys on histological analysis (EPACC 2, IQR 2-2; STD 0.5 IQR 0-2, p=0.02), but there were no differences in the amount of cellular damage on direct visualization (EPACC 2, IQR 0-3; STD 0, IQR 0-2, p=0.16). There were no differences in the histologic analysis of small bowel, large bowel, or spinal cord.

The intent of this study was to determine if partial augmentation of proximal blood pressure using an automated endovascular aortic balloon catheter in a model of vasodilatory shock could serve as a resuscitative adjunct by improving hemodynamics to the heart, lung, and brain while maintaining adequate flow to clear distal ischemic metabolites and perfuse distal vascular beds. The feasibility of this approach was demonstrated using an automated syringe pump precisely controlling balloon volume in response to proximal blood pressure and aortic flow. Using an aggressive threshold for endovascular support, improvements in fluids and vasopressor requirements have been demonstrated without increasing the overall ischemic burden. EPACC improved both the average blood pressure proximal to the balloon as well as the duration of time within the predefined target blood pressure range despite having similar blood pressure goals and fluid and vasopressor resuscitation requirements. Although serum creatinine was increased with EPACC, there were no differences in the extent of renal injury on histologic analysis.

Vasodilatory shock from ischemia reperfusion injuries is common after procedures requiring complete aortic occlusion. Similar to septic shock states, patients are often unresponsive to initial early interventions and may require large volumes of crystalloid infusions and high doses of vasopressor medications to optimize perfusion to the heart and brain. Often, these interventions themselves can be harmful, leading to pulmonary edema, heart failure, cerebral edema, and ischemia to distal organs and limbs from excessive vasoconstriction. In the most extreme cases, a patient's cardiovascular system can be unresponsive to any intervention. This refractory state leads to persistent hypotension, electrolyte and glucose metabolism abnormalities, multiorgan ischemia, and death. While the clinical consensus on the resuscitation algorithms and medications used to treat shock are continually refined, there has been no recent innovation proposed for refractory states. In these scenarios, EPACC may be a viable adjunct. Endovascular techniques and tools have improved greatly over the past 20 years with a steady advance towards smaller devices and greater functionality. For example, small 7 Fr catheters are now being used routinely to arrest hemorrhage in exsanguinating trauma patients with promising results. The development of these low profile catheters has paved the way for endovascular techniques as an adjunct to standard critical care resuscitation.

Using a vasodilatory hyperdynamic model of shock partial aortic occlusion has been demonstrated to augment proximal pressure and decrease resuscitation requirements while maintaining a sufficient level of distal perfusion to clear ischemic metabolites at a rate similar to standard critical care. With the exception of cardiac and neurogenic shock, most types of shock exhibit a hyperdynamic cardiac output state after even minimal intravascular volume restoration. This increased cardiac demand can be undermined by poor coronary artery perfusion during a diastolic filling period that is characterized by low diastolic blood pressures. Therefore, excessive cardiac output is not only insufficient to perfuse distal tissues and minimize ischemia but also results in increased cardiac work in the setting of compromised coronary perfusion. This vicious cycle can lead to cardiovascular collapse.

Current therapeutic adjuncts for shock states can only address global hemodynamics, and therefore large amounts of crystalloids and high doses of vasopressors may be required before perfusion to the heart is optimized. EPACC offers a novel intervention to augment standard critical care. Although distal aortic flow is attenuated by EPACC, the animals were still able to clear the large lactate burden as well as the STD group. This result suggests that excessive aortic flow above weight-based norms to distal tissue beds does not necessarily hasten clearance of ischemic by-products. This is a critical finding when understanding the potential safety of this novel therapy, namely that attenuating aortic flow back to a normal pre-injury level with EPACC does not result in additional ischemia to injured tissues. In essence, a hyperemic aortic flow state in response to ischemia is not necessarily beneficial and may actually represent a pathologic response to injury. Conversely, this suggests that attenuating aortic flow with EPACC towards a more physiologic range in the context of a hyperdynamic cardiac state may be of benefit by reducing overall cardiac work without incurring additional distal ischemic debt.

Beyond attenuated aortic flow, EPACC inherently produces a lower mean arterial pressure below the level of partial occlusion. In this study, EPACC animals consistently demonstrated a significantly lower blood pressure distal to the balloon compared to conventional critical care. This finding suggests that the distal pressures maintained with EPACC were sufficient to clear ischemic metabolites and that traditional diastolic blood pressure goals of greater than 65 mmHg for shock may not be required to maintain adequate tissue perfusion after source control has been achieved.

In settings of severe vasodilatory shock, maintaining adequate blood pressure is often difficult despite mobilizing maximal resources and effort for an individual patient. We have demonstrated that even with similar blood pressure goals, EPACC was able to improve the average mean arterial blood pressure throughout the period of critical care when compared to STD. These findings may be the result of two separate phenomenon noted with EPACC. First, EPACC is capable of near instantaneous adjustments of balloon volume on a second-to-second basis in response to blood pressure fluctuations. Unlike the administration of intravenous crystalloids or intravenous vasopressor medications that take time to be delivered and have their effect, the mechanical augmentation of blood pressure is instantaneous. Thus, the greater precision of EPACC interventions combined with their rapid effect result in numerous minute adjustments that create hemodynamic consistency. This likely accounts for the greater percentage of time within the target blood pressure range seen with EPACC. The second possible explanation for the improved hemodynamics within the EPACC group is a preferential effect on the coronary artery perfusion that arises from increased afterload near the aortic root that is achieved without increasing arteriolar vasoconstriction with vasopressors. Therefore, EPACC may offer a critical adjunct to IV fluids and vasopressors by optimizing coronary perfusion.

In addition to its general applicability to shock, EPACC may also have a distinct role in the resuscitation of ischemia-reperfusion injuries (IRI) following aortic occlusion by controlling the washout of distal ischemic metabolites. Although a multisystem trauma victim with IRI is a fairly specific patient, the advent of REBOA for trauma is increasing the incidence of IRI from the profound distal ischemia. These ischemic tissues manifest inflammatory cytokines, but can also result in hyperkalemia during reperfusion with resultant cardiac depression. While both groups of animals in the present study had profound IRI, EPACC controlled distal flow for the majority of the critical care phase as evidenced by lower aortic flow rates. This gradual return to baseline aortic flow rates may have slowed the washout of ischemic metabolites and served to minimize ongoing injury that occurs as a direct result of reperfusion of damaged tissues. Prior work has demonstrated that during ischemia and reperfusion, the injury to the tissue beds are a result of not only the initial ischemia, but also of the reaction of the ischemic tissues to the reintroduction of oxygenated blood. This reintroduction of oxygen into tissues results in the rapid development of reactive oxygen species, opening of the MPT pore of mitochondria that were already damaged during the original ischemia, an influx of calcium into the cell, routine endothelial dysfunction with increased vasodilation, and the generation of a larger inflammatory response. It remains unclear at this time whether a slower reintroduction of oxygenated blood to distal tissues will be beneficial, or the nuances of when and how that reintroduction should occur. Nevertheless, the present study demonstrates that EPACC has the functionality to tightly control distal reperfusion. This controlled reintroduction of flow may ultimately serve to minimize the reperfusion injury that ensues.

The resuscitation of a critically ill patient represents a significant demand on medical facilities, consuming physical resources as well as cognitive capacity. Not only is this demand substantial in the moment, but is frequently sustained for extended periods. In resource limited environments, a single critically ill patient can overwhelm available resources, precluding high quality care in the context of multiple critically ill patients. Therefore, strategies to minimize utilization of these scarce resources will inherently enable higher quality care for more patients. EPACC addresses several of these key consideration for critical care environments. First, EPACC may limit reliance on large volume crystalloid administration and the need for prolonged infusion of vasoactive agents. This is of particular relevance for care in resource poor scenarios, where the ability to maintain large volumes of crystalloid or vasoactive drugs is not feasible. Second, through the use of automation, EPACC can provide maintenance of hemodynamics without the reliance on continuous involvement of the provider, effectively offloading the cognitive requirements needed to care for critically injured patients. This affords the opportunity to provide sustained high level care to multiple patients simultaneously. Finally, this technology enables transitions of care or transport of patients without the need for extensive resources. This applies to scenarios of prolonged critical care transport from rural medical facilities or austere military environments.

While great improvements have been made in the care of critically ill patients through protocolized algorithms, human error and system constraints still result in failure to adequately resuscitate. For example, a patient who cannot tolerate large fluid boluses is susceptible to heart failure or pulmonary edema, while failing to provide sufficient intravascular volume to optimize cardiovascular performance is equally as deleterious.

The development of EPACC for critical care has been driven by the developing need for minimized material requirements for the prolonged field care scenarios that can exist for military physicians and practitioners, and therefore an aggressive amount of mechanical pressure augmentation was chosen in an attempt to maximize the material benefit, while potentially incurring some ongoing distal ischemia. This strategy where fluid administration is not initiated until native aortic flow is less than 80% of weight based norms resulted in a dramatic reduction in fluid and vasopressor requirements, but was met with increasing creatinine. The increase in creatinine was not associated with a change in histology between groups or an difference in the urine:serum n-gal concentration—a marker of direct renal injury. The increase in creatine may be secondary to the expected decrease in renal blood flow and subsequent decrease in filtration. A small but not significant increase in the urine: serum n-gal ratio may also be early evidence of renal injury that is either not yet apparent given the short duration of the study or not significant due to the small number of animals in the study. Future long term survival studies as well as dose response curves to establish the optimal minimum aortic flow threshold beyond which fluid and vasopressor administration are re-instated are necessary to fully realize the potential and safety of EPACC.

There are several limitations to the current study. First, this was a limited survival study with a total experimental time of only 6 hours. Many physiologic consequences of trauma and from interventions are often delayed. It may be that critical differences between groups with respect to physiology or histology would manifest with studies of longer duration. A second limitation is that only a single "dose" of EPACC was tested in this study. Like any intervention, EPACC can be adjusted in the amount of balloon support provided prior to the addition of intravenous fluids or vasopressors. For this study, a "dose" of 80% of weight adjusted baseline aortic flow was chosen. However, as described above, other minimum aortic flow thresholds may be used depending on the specific patient's condition. Finally, only one shock state was tested in this study. It is possible that the shock state from ischemia-reperfusion is distinct from other etiologies of shock. Therefore, future studies are needed to fully understand the potential utility of endovascular support for other types of shock such as septic shock. These limitations notwithstanding, the current manuscript is the first description of a fully automated critical care platform that incorporates endovascular support in order to minimize material requirements for patients in shock from ischemia reperfusion injury. Furthermore, it represents a novel therapeutic approach to patients in refractory shock and may prove advantageous in lesser degrees of physiologic derangement to minimize the morbidity and mortality associated with conventional treatments.

Thus, the addition of EPACC versus an automated critical care platform alone significantly reduced material requirements for resuscitation while increasing both the average proximal MAP and the duration of time at goal blood pressure. Although EPACC did result in a higher serum creatinine concentration by the end of the study, there were no differences in markers of renal injury or histology between groups.

While various illustrative embodiments of the disclosure are described above, it will be apparent to one skilled in the art that various changes and modifications may be made therein without departing from the disclosure. The appended claims are intended to cover all such changes and modifications that fall within the true scope of the disclosure.

What is claimed:

1. An automated endovascular perfusion augmentation system, the system comprising:
a catheter having a proximal end portion and a distal end portion, the distal end portion configured for placement within an aorta of a patient;
an expandable aortic blood flow regulation device disposed on the distal end portion of the catheter for placement within the aorta, the expandable aortic blood flow regulation device configured to expand to restrict blood flow through the aorta and to contract;
a catheter controller unit coupled to the proximal end portion of the catheter and configured to cause the expandable aortic blood flow regulation device to expand and contract in the aorta;
one or more sensors configured to measure physiological information indicative of blood flow through the aorta; and
a non-transitory computer readable media having instructions stored thereon, wherein the instructions, when executed by a processor coupled to the one or more sensors, cause the processor to compare the measured physiological information with a target physiological range such that the catheter controller unit automatically adjusts expansion and contraction of the expandable aortic blood flow regulation device to adjust an amount of blood flow through the aorta if the measured physiological information falls outside the target physiological range.

2. The system of claim 1, wherein the expandable aortic blood flow regulation device comprises a balloon configured to be inflated to expand to restrict blood flow through the aorta, and wherein the catheter controller unit comprises a syringe pump configured to inflate or deflate the balloon to adjust the amount of blood flow through the aorta if the measured physiological information falls outside the target physiological range.

3. The system of claim 1, wherein the expandable aortic blood flow regulation device comprises:
a balloon configured to be inflated to occlude blood flow through the aorta; and
one or more wires configured to surround the balloon, the one or more wires further configured to be tightened to indent the balloon to permit blood flow around the balloon,
wherein the catheter controller unit comprises a syringe pump configured to inflate or deflate the balloon, and
wherein the catheter controller unit is further configured to shorten or lengthen the one or more wires to tighten or loosen the one or more wires surrounding the balloon to adjust the amount of blood flow through the aorta if the measured physiological information falls outside the target physiological range.

4. The system of claim 3, wherein the catheter controller unit shortens or lengthens the one or more wires via at least one of a stepper motor or a motorized arm configured to shorten or lengthen the one or more wires against a fixed point on the catheter.

5. The system of claim 1, wherein the expandable aortic blood flow regulation device comprises:
a wire framework configured to radially expand or contract from a center axis of the catheter; and
an aortic blood flow regulation sail comprising a thin membrane, the aortic blood flow regulation sail configured to surround a portion of the wire framework,
wherein the catheter controller unit is configured to shorten or lengthen the wire framework to radially expand or contract the aortic blood flow regulation sail to adjust the amount of blood flow through the aorta if the measured physiological information falls outside the target physiological range.

6. The system of claim 5, wherein the catheter controller unit shortens or lengthens the wire framework via at least one of a stepper motor or a motorized arm configured to shorten or lengthen the wire framework against a fixed point on the catheter.

7. The system of claim 1, wherein the expandable aortic blood flow regulation device comprises:
a non-compliant balloon having one or more windows; and
a compliant balloon configured to be enclosed within the non-compliant balloon,
wherein the catheter controller unit comprises a syringe pump configured to inflate or deflate the compliant balloon such that the compliant balloon is extruded through the one or more windows of the non-compliant balloon to adjust the amount of blood flow through the aorta if the measured physiological information falls outside the target physiological range.

8. The system of claim 1, wherein one of the one or more sensors is disposed on the catheter distal to the expandable aortic blood flow regulation device and is configured to measure physiological information indicative of blood pressure in the aorta distal to the expandable aortic blood flow regulation device.

9. The system of claim 1, wherein one of the one or more sensors is disposed on the catheter proximal to the expandable aortic blood flow regulation device and is configured to measure physiological information indicative of blood pressure in the aorta proximal to the expandable aortic blood flow regulation device.

10. The system of claim 1, wherein the one or more sensors are configured to measure physiological information indicative of blood flow through the aorta including at least one of heart rate, respiratory rate, aortic blood flow proximal or distal to the expandable aortic blood flow regulation device, blood temperature, pressure within the expandable aortic blood flow regulation device, cardiac output of the patient, carotid blood flow, pulmonary pressures, peripheral vascular resistance, or intracranial pressure.

11. The system of claim 1, wherein the one or more sensors are configured to measure physiological information indicative of blood flow through the aorta by measuring at least one of lactate level, cortisol level, reactive oxygen species level, or pH, of a fluid of the patient.

12. The system of claim 1, further comprising a second expandable aortic blood flow regulation device disposed on the distal end portion of the catheter proximal to the expandable aortic blood flow regulation device for placement within the aorta, the second expandable aortic blood flow regulation device coupled to the catheter controller unit and configured to expand to restrict blood flow through the aorta and to contract,
wherein the expandable aortic blood flow regulation device and the second expandable aortic blood flow regulation device are configured to be spaced apart such that the expandable aortic blood flow regulation device is placed in a zone of the aorta, and the second expandable aortic blood flow regulation device is placed in a different zone of the aorta.

13. The system of claim 12, wherein at least one of the one or more sensors is positioned distal to the expandable aortic blood flow regulation device, in between the expandable aortic blood flow regulation device and the second expandable aortic blood flow regulation device, or proximal to the second expandable aortic blood flow regulation device.

14. The system of claim 1, further comprising an external central processing unit operatively coupled to the one or more sensors and the catheter controller unit, the external central processing unit comprising the processor and configure to transmit information indicative of whether the measured physiological information falls outside the target physiological range to the catheter controller unit.

15. The system of claim 14, wherein the external central processing unit transmits the information to the catheter controller unit via at least one of WiFi, Bluetooth, Wixel-based communication, or cellular communication.

16. The system of claim 1, further comprising an automated pump configured to deliver intravenous medication to the patient, wherein the instructions, when executed by the processor coupled to the one or more sensors, cause the processor to compare the measured physiological information with a target physiological range such that the automated pump delivers intravenous medications to the patient to modulate patient physiology based on the comparison.

17. The system of claim 1, further comprising an automated pump configured to deliver intravenous fluids and blood products to the patient, wherein the instructions, when executed by the processor coupled to the one or more sensors, cause the processor to compare the measured physiological information with a target physiological range such that the automated pump delivers intravenous fluids or blood products to the patient to modulate patient physiology based on the comparison.

18. A method for automatically, dynamically regulating the degree of aortic blood flow regulation for endovascular perfusion augmentation, the method comprising:
introducing a distal end portion of a catheter comprising an expandable aortic blood flow regulation device within an aorta of a patient;
expanding the expandable aortic blood flow regulation device to restrict blood flow through the aorta;
measuring physiological information indicative of blood flow through the aorta via one or more sensors;
comparing the measured physiological information with a target physiological range; and
adjusting expansion and contraction of the expandable aortic blood flow regulation device to adjust an amount of blood flow through the aorta if the measured physiological information falls outside the target physiological range.

19. The method of claim 18, wherein the expandable aortic blood flow regulation device comprises a balloon configured to be inflated to expand to restrict blood flow through the aorta, and wherein expanding or contracting the expandable aortic blood flow regulation device comprises inflating or deflating the balloon via a syringe pump.

20. The method of claim 18, wherein measuring physiological information indicative of blood flow through the aorta via one or more sensors comprises measuring at least one of heart rate, respiratory rate, aortic blood flow proximal or distal to the expandable aortic blood flow regulation device, blood temperature, pressure within the expandable aortic blood flow regulation device, cardiac output of the patient, carotid blood flow, pulmonary pressures, peripheral vascular resistance, or intracranial pressure.

* * * * *